(12) United States Patent
Norton et al.

(10) Patent No.: US 7,517,959 B2
(45) Date of Patent: Apr. 14, 2009

(54) SOCS3 PROTEINS

(75) Inventors: Raymond Stanley Norton, Ivanhoe (AU); Jeffrey James Babon, North Carlton (AU); Sandra Elaine Nicholson, Williamstown (AU); Nicos Anthony Nicola, Mont Albert (AU); Edward James McManus, Clifton Hill (AU); Manuel Baca, Viewbank (AU); Shenggen Yao, Doncaster (AU)

(73) Assignee: Walter and Eliza Hall Institute of Medical Research, Parkville (AU)

( * ) Notice: Subject to any disclaimer, the term of this patent is extended or adjusted under 35 U.S.C. 154(b) by 0 days.

(21) Appl. No.: 11/598,212

(22) Filed: Nov. 9, 2006

(65) Prior Publication Data

US 2007/0179089 A1    Aug. 2, 2007

(30) Foreign Application Priority Data

Nov. 11, 2005    (AU) ............................. 2005906285

(51) Int. Cl.
C07K 14/46    (2006.01)
A61K 38/17    (2006.01)

(52) U.S. Cl. ...................................... 530/350; 530/399

(58) Field of Classification Search ....................... None
See application file for complete search history.

(56) References Cited

U.S. PATENT DOCUMENTS

| | | | |
|---|---|---|---|
| 5,807,746 | A | 9/1998 | Lin et al. |
| 6,043,339 | A | 3/2000 | Lin et al. |
| 6,248,558 | B1 | 6/2001 | Lin et al. |
| 6,432,680 | B1 | 8/2002 | Lin et al. |
| 6,495,518 | B1 | 12/2002 | Hawiger et al. |
| 6,780,843 | B2 | 8/2004 | Lin et al. |

FOREIGN PATENT DOCUMENTS

| | | |
|---|---|---|
| WO | WO 94/04686 | 3/1994 |
| WO | WO 99/49879 | 10/1999 |
| WO | WO 01/37821 | 5/2001 |
| WO | WO 2005/086800 | 9/2005 |

OTHER PUBLICATIONS

Skolnick et al. From genes to protein structure and function: novel applications of computational approaches in the genomic era. Trends in Biotech 18(1): 34-39, 2000.*
Bork, A. Powers and pitfalls in sequence analysis: the 70% hurdle. Genome Res 10: 398-400, 2000.*
Doerks et al. Protein annotation: detective work for function prediction. Trends in Genetics 14(6): 248-250, 1998.*
Smith et al. The challenges of genome sequence annotation or "The devil is in the details". Nature Biotech 15: 1222-1223, 1997.*
Brenner, S.E. Errors in genome function. Trends in Genetics 15(4): 132-133, 1999.*
Bork et al. Go hunting in sequence databases but watch out for the traps. Trends in Genetics. 12(10): 425-427, 1996.*
Wells. J.A. Additivity of mutational effects in proteins. Biochemistry 29 (37): 8509-8517, 1990.*
Ngo et al. Computational complexity, protein structure prediction, and the Levinthal paradox. The Protein Folding Problem and Tertiary Structure Prediction, pp. 492-495, 1994.*
Martens et al. The suppressor of cytokine signaling (SOCS)-7 interacts with the actin cytoskeleton through vinexin. Exp Cell Rres 298: 239-248, 2004.*
Alexander, et al., "The Role of Suppressors of Cytokine Signalling (SOCS) Proteins in Regulation of the Immune Response," (2004) Annu. Rev. Immunol. 22:503-529.
Babon, et al., "Secondary structure assignment of mouse SOSC3 by NMR defines the domain boundaries and identifies an unstructured insertion in the SH2 domain," (2005) FEBS Journal, pp. 1-11.
Babon, et al., "The Structure of SOCS3 Reveals the Basis of the Extended Sh2 Domain Function and Identifies an Unstructured Insertion That Regulates Stability," (2006) Molecular Cell, 22:205-216.
Ball, et al., "Conformational Constraints: Nonpeptide β-Turn Mimics," (1990) J. Mol. Recognition 3:55.
Becker, S et al. Three-dimensional structure of the Stat3β homodimer bound to DNA (1998) Nature 394:145-151.
Beddell, "Designing Drugs to Fit a Macromolecular Receptor," (1985) Chem. Soc. Reviews 279.
Bergamin, et al., "Structural Basis for Phosphotyrosine Recognition by Suppressor of Cytokine Signaling-3," (2006) Structure 14:1285-1292.
Bohm, et al., "Rapid Empirical Scoring Functions in Virtual Screening Applications," (1999) M. Med. Chem. Res. 9: 445.
Brescia, et al., "Letter to the Editor: Assignment of Backbone $^1$H, $^{13}$C, and $^{15}$N resonances of human Grb7-SH2 domain in complex with a phosphorylated peptide ligand," (2002) J Biomol NMR. 23:77-78.
Chen, et al., "Pim serine/threonin kinases regulatethe stability of Socs-1 protein," (2002) Proc Natl Acad Sci USA. 99:2175-2180.
Cornilescu, et al., "Protein backbone angle restraints from searching a database for chemical shift and sequence homology," (1999) J Biomol NMR. 13:289-302.
Croker, et al., "SOCS3 negatively regulates IL-6 signaling in vivo," (2003) Nat Immunol. 4:540-545.
Croker, et al., "SOCS3 Is a Critical Physiological Negative Reglator of G-CSF Signaling and Emergency Granulopoiesis," (2004) Immunity 20:153-165.

(Continued)

*Primary Examiner*—Bridget E Bunner
(74) *Attorney, Agent, or Firm*—Carol L. Francis; Bozicevic, Field & Francis LLP

(57) ABSTRACT

The present invention relates to the identification of a PEST motif in Suppressor of Cytokine Signalling (SOCS) proteins, the deletion/inactivation of which has been found to increase the stability of the protein whilst maintaining at least one biological activity of the protein. Such SOCS proteins with deleted/inactivated PEST motifs can be used in gene and protein therapy procedures to provide a more stable SOCS protein when compared to the native protein. The present invention also relates to the characterization of the structure of SOCS proteins, and methods of using this structural information to identify compounds which modulate the activity of SOCS.

11 Claims, 8 Drawing Sheets

OTHER PUBLICATIONS

Figure 1:
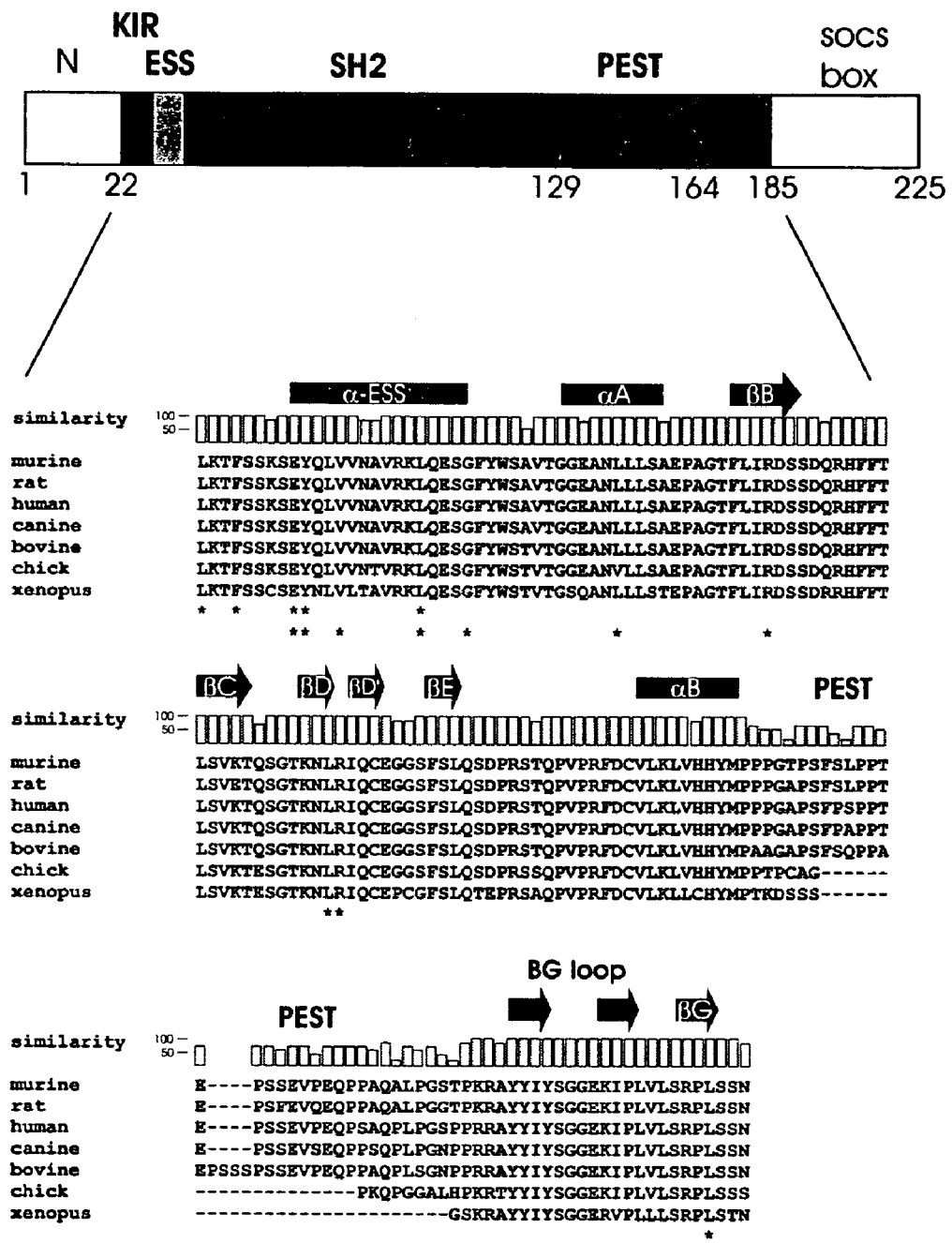

De Esch, et al., "Development of a Pharmacophore Model for Histamine H3 Receptor Antagonists, Using the Newly Developed Molecular Modeling Program SLATE," (2001) J. Med. Chem. 44:1666-1674.

Delaglio, et al., NMRPipe: A multidimentional spectral processing system based on UNIX pipes, (1995) J Biomol NMR 6:277-293.

Ewing, et al., DOCK 4.0: Search strategies for automated molecular docking of flexible molecule databases, (2001) J. Comput-Aid. Mol. Design 15: 411.

Freidinger, "Non-peptide ligands for peptide receptors," (1989) Trends Pharmacol. Sci. 10:270.

Friederichs, et al., "Interleukin-6-induced proliferation of pre-B cells mediated by receptor complexes lacking the SHP2/SOCS3 recruitment sites revisited," (2001) Eur J Biochem. 268:6401-6407.

Gane, et al., "Recent advances in structure-based rational drug design," (2000) Curr. Opinion Struct. Biol. 10: 401.

Good, "Structure-based virtual screening protocols," (2001) Current Opinion in Drug Disc. Devel. 5, 301.

Goodford, "Drug Design by the Method of Receptor Fit," (1984) J. Med. Chem. 27: 557.

Goodford, "A Computational Procedure for Determining Energetically Favorable Binding Sites on Biologically Important Macromolecules," (1985) J. Med. Chem. 28:849.

Grucza, et al., "SH2 Domains: From Structure to Energetics, A Dual Approach to the Study of Structure-Function Relationships," (1999) Med Res Rev. 19:273-293.

Harper, et al., "Helix Stop Signals in Proteins and Peptides: The Capping Box," (1993) Biochemistry 32:7605-7609.

Hilton, "Negative regulators of cytokine signal transduction," (1999) Cell Mol Life Sci. 55:1568-1577.

Hilton, et al., "Twenty proteins containing a C-terminal SOCs box form five structural classes," (1998) Proc Natl Acad Sci USA 95:114-119.

Hirschmann, et al. "De Novo Design and Synthesis of Somatostatin Non-Peptide Peptidomimetics Utilizing β-D-Glucose as a Novel Scaffolding," (1993) J. Am. Chem. Soc. 115:12550-12568.

Hol, "Protein Crystallography and Computer Graphics—toward Rational Drug Design," (1986) Angew. Chem. 25: 767.

Holm, et al., "Dali: a network tool for protein structure comparison," (1995) Trends Biochem Sci. 478-480.

Hortner, et al., "A new high affinity binding site for suppressor of cytokine signaling-3 on the erythropoietin receptor," (2002) Eur J Biochem. 269:2516-2526.

Hortner, et al., "Suppressor of Cytokine Signaling-3 Is Recruited to the Activated Granulocyte-Colony Stimulating Factor Receptor and Modulates its Signal Transduction," (2002) J Immunol. 169:1219-1227.

Horton, et al., "Engineering hybrid genes without the use of restriction enzymes: gene splicing by overlap extension," (1989) Gene 77:61-68.

Ihle, et al. "Signaling Through the Hematopoietic Cytokine Receptors," (1995) Annu Rev Immunol. 13:369-398.

Jo, et al., "Intracellular protein therapy with SOCS3 inhibits inflammation and apoptosis," (2005) Nat Med. 11:892-898.

Jones, et al., "Improved Methods for Building Protein Models in Electron Density Maps and the Location of Errors in these Models," (1991) Acta Cryst. A47:110-119.

Kamura, et al., "The Elongin BC complex interacts with the conserved SOCS-box motif present in members of the SOCS, ras, WD-40 repeat, and ankyrin repeat families," (1998) Genes Dev. 12:3872-3881.

Kamura, et al., "VHL-box and SOCS-box domains determine binding specificity for Cul2-Rbx1 and Cul5-Rbx2 modules of ubiquitin ligases," (2004) Genes Dev. 18:3055-3065.

Kile et al., "The SOCS box: a tale of destruction and degradation," (2002) Trends Biochem Sci. 27:235-241.

Kimura, et al., "SOCS3 Is a Physiological Negative Regulator for Granulopoiesis and Granulocyte Colony-stimulating Factor Receptor Signaling," (2004) J Biol Chem. 279:6905-6910.

Koradi et al., "MOLMOL: A program for display and analysis of macromolecular structures," (1996) J Mol Graph. 14:51-55.

Kuntz et al., "A Geometric Approach to Macromolecule-Ligand Interactions," (1982) J. Mol. Biol. 161: 269.

Ladbury et al., "Measurement of the binding of tyrosyl phosphopeptides to SH2 domains: A reappraisal," (1995) Proc Natl Acad Sci USA. 92:3199-3203.

Langer, et al., "Virtual Screening: An Effective Tool for the Lead Structure Discovery?," (2001) Current Pharmaceutical Design 7: 509.

Laskowski, et al., "AQUA and PROCHECK-NMR: programs for checking the quality of protein structures solved by NMR," (1996) J Biomol NMR. 8:477-486.

Leonard, et al., "JAKS and STATS: Biological Implications," (1998) Annu Rev Immunol. 16:293-322.

Marine, et al., "SOCS3 Is Essential in the Regulation of Fetal Liver Erythropoiesis," (1999) Cell 98:617-627.

Miller, "Retrovirus Packaging Cells," (1990) Human Gene Therapy 1:5-14.

Mills et al., (1997) "An automated method for predicting the positions of hydrogen-bonding atoms in binding sites," J Comp Aided Mol Des 11:229-242.

Mills, et al., "SLATE: A method for the superposition of flexible ligands," (2001) J Comp Aided Mol Des 15:81-96.

Mizushima, et al., "pEF-BOS, a powerful mammalian expression vector," (1990) Nucleic Acids Res. 18:5322.

Morgan, et al., "Approaches to the Discovery on Non-Peptide Ligands or Peptide Receptors and Peptidases," (1989) Ann. Rep. Med. Chem. 24:243.

Mori, et al., "SOCS3 deficiency in the brain elevates leptin sensitivity and confers resistance to diet-induced obesity," (2004) Nat Med. 10:739-743.

Munoz, et al., "The hydrophobic-staple motif and a role for loop-residues in α-helix stability and protein folding," (1995) Nat Struct Biol. 2:380-385.

Naka, et al., "Structure and function of a new STAT-induced STAT inhibitor," (1997) Nature 387:924-929.

Neidhardt, et al., "Culture Medium for Enterobacteria," (1974) J Bacteriol. 119:736-747.

Nicholson, et al., "Mutational analyses of the SOCS proteins suggest a dual domain requirement but distinct mechanisms for inhibition of LIF and IL-6 signal transduction," (1999) EMBO J. 375-385.

Nicholson, et al., "Suppressor of cytokine signaling-3 preferentially binds to the SHP-2-binding site on the shared cytokine receptor subunit gp130," (2000) Proc Natl Acad Sci USA. 97:6493-6498.

Ohya, et al., "SOCS-1/JAB/SSI-1 Can Bind to and Suppress Tec Protein-tyrosine Kinase," (1997) The Journal of Biological Chemistry, vol. 272, No. 43, pp. 27178-27182.

Okazaki, et al., "Analysis of the mouse transcriptome based on functional annotation of 60,770 full-length cDNAs," (2002) Nature 420:563-573.

Pellecchia et al., "Pilus chaperone FimC-adhesin FimH interactions mapped by TROSY-NMR," (1999) Nat Struct Biol. 6:336-339.

Perkins, et al., "Molecular surface-volume and property matching to superpose flexible dissimilar molecules," (1995) J Comp Aided Mol Des 9:479-490.

Rarey, et al., "A Fast Flexible Docking Method using an Incremental Construction Algorithm," (1996) J. Mol. Biol. 261: 470.

Rechsteiner, et al., "PEST sequences and regulation by proteolysis," (1996) Trends Biochem Sci. 21:267-271.

Roberts, et al., "Placental defects and embryonic lethality in mice lacking suppressor of cytokine signaling 3," (2001) Proc Natl Acad Sci USA. 98:9324-9329.

Rogers, et al., "Amino Acid Sequences Common to Rapidly Degraded Proteins: The PEST Hypothesis," (1986) Science 234:364-368.

Sasaki, et al., "Cytokine-inducible SH2 protein-3 (CIS3/SOCS3) inhibits Janus tyrosine kinase by binding through the N-terminal kinase inhibitory region as well as SH2 domain," (1999) Genes Cells 4:339-351.

Sasaki, et al., "CIS3/SOCS-3 Suppresses Erythropoietin (EPO) Signaling by Binding the EPO Receptor and Jak2*," (2000) J Biol Chem. 275:29338-29347.

Sasaki, et al., "The N-terminal Truncated Isoform of SOCS3 Translated from an Alternative initiation AUG Codon under Stress Conditions Is Stable Due to the Lack of a Major Ubiquitination Site, Lys-6," (2003) J Biol Chem. 278:2432-2436.

Schmitz, et al., "SOCS3 Exerts Its Inhibitory Function on Interleukin-6 Signal Transduction through the SHP2 Recruitment Site of gp130*," (2000) J Biol Chem. 275:12848-12856.

Sheridan, et al., "New Methods in Computer-Aided Drug Design," (1987) Acc. Chem Res. 20: 322.

Shi, et al., "Suppressor of Cytokine Signaling 3 Is a Physiological Regulator of Adipocyte Insulin Signaling," (2004) J Biol Chem. 279:34733-34740.

Smith, et al., "De Novo Design, Synthesis, and X-ray Crystal Structures of Pyrrolindone-Based β-Strand Peptidomimetics," (1994) J. Am. Chem. Soc. 116:9947-9962.

Smith, et al., "Pyrrolindone-Based HIV Protease Inhibitors, Design, Synthesis, and Antiviral Activity: Evidence for Improved Transport," (1995) J. Am. Chem. Soc. 117:11113-11123.

Starr, et al., "A family of cytokine-inducible inhibitors of signalling," (1997) Nature 387:917-921.

Verlinde, et al., "Structure-based drug design: progress, results and challenges," (1984) Structure 2: 577.

Waksman, et al., "Binding of a High Affinity Phosphotyrosyl Peptide to the Src SH2 Domain: Crystal Structures of the Complexed and Peptide-free Forms," (1993) Cell 72:779-790.

Walters, et al., "Virtual screening—an overview," (1998) Drug Discovery Today 3: 160.

Ward, et al., "Direct binding of Shc, Grb2, SHP-2 and p40 to the murine granulocyte colony-stimulating factor receptor," (1998) Biochim Biophys Acta. 1448:70-76.

Yasukawa, et al. "The JAK-binding protein JAB inhibits Janus tyrosine kinase activity through binding in the activation loop," (1999) EMBO J. 18:1309-1320.

Yasukawa, et al. "IL-6 induces an anti-inflammatory response in the absence of SOCS3 in macrophages," (2003) Nat Immunol. 4:551-556.

Yoshimura, et al. "A novel cytokine-inducible gene CIS encodes an SH2-containing protein that binds to tyrosine-phosphorylated interleukin 3 and erythropoietin receptors," (1995) EMBO J. 14:2816-2826.

Yoshimura, et al. "Negative regulation of cytokine signaling and immune responses by SOCS proteins," (2005) Arthritis Res Ther. 7:100-110.

Zhang et al. "The conserved SOCs box motif in suppressors of cytokine signaling binds to elongins B and C and may couple bound proteins to proteasomal degradation," (1999) Proc Natl Acad Sci USA 96:2071-2076.

Lang, R., et al. SOCS3 regulates the plasticity of gp130 signaling. Nature Immunology. 2003, vol. 4, No. 6, pp. 546-550.

* cited by examiner

A

B

A

B

A

B

SOCS3 PROTEINS

FIELD OF THE INVENTION

The present invention relates to the identification of a PEST motif in Suppressor of Cytokine Signalling (SOCS) proteins, the deletion/inactivation of which has been found to increase the stability of the protein whilst maintaining at least one biological activity of the protein. Such SOCS proteins with deleted/inactivated PEST motifs can be used in gene and protein therapy procedures to provide a more stable SOCS protein when compared to the native protein. The present invention also relates to the characterization of the structure of SOCS proteins, and methods of using this structural information to identify compounds which modulate the activity of SOCS.

TABLES

The present application incorporates by reference Table 1 which is contained as the electronic file "table1.txt" on duplicate discs filed concurrently herewith, which compact discs are labeled "Atty Docket RICE-059 Tables Copy 1" and "Atty Docket RICE-059 Tables Copy 2". The details of Table 1 are further described later in the disclosure.

These compact discs were created on Nov. 9, 2006. The electronic file has the following size: 3,964 kilobytes.

BACKGROUND OF THE INVENTION

Cytokine signalling involves a cascade of intracellular intermediates activated by tyrosine phosphorylation and is tightly regulated. Signalling is initiated following cytokine binding to specific cell-surface receptors, inducing receptor oligomerisation. This allows transphosphorylation of receptor-associated Janus kinases (JAKs), which in turn phosphorylate the intracellular subunits of the receptor at specific tyrosine residues (Ihle et al., 1995). The phosphorylated tyrosines then act as docking sites for members of the signal transduction and activators of transcription (STAT) family. The STAT family is phosphorylated by the JAKs following docking, whereupon they dimerise and translocate into the nucleus, to function as transcription factors (Leonard and O'Shea, 1998).

The Suppressor of cytokine signalling proteins, SOCS1-7 and cytokine-inducible SH2-containing protein (CIS) (Starr et al., 1997; Yoshimura et al., 1995, Naka et al., 1997), not only directly disrupt the cytokine-induced intracellular signalling cascade, but also affect signal transduction by accelerating the turnover of signalling intermediates through the SOCS box (Hilton et al., 1998), which interacts with elonginB/C (Zhang et al., 1999) and cullin5 (Kamura et al., 2004) to form an E3 ubiquitin ligase. Transcription of SOCS1-3 and CIS, is upregulated following STAT activation (Hilton, 1999) and these SOCS proteins therefore control the duration of the signalling response via a negative feedback mechanism.

Socs3 knockout mice die in utero due to placental defects (Roberts et al., 2001). However, conditional knockout studies have illustrated that SOCS3 plays an indispensable role in regulating the inflammatory response and metabolism. For example, SOCS3 is essential in controlling the response to IL-6 (Croker et al., 2003; Lang et al., 2003; Yasukawa et al., 2003) and G-CSF (Croker et al., 2004; Kimura et al., 2004). Mice with haematopoietic deletion of Socs3 display a number of inflammatory disorders (Croker et al., 2004) and are acutely sensitive to G-CSF stimulation. Conditional knockout of Socs3 in neural cells leads to a severe loss in body-weight via enhanced leptin signalling (Mori et al., 2004), whilst SOCS3 deficient adipocytes are protected against TNFα-induced insulin resistance (Shi et al., 2004). Intracellular delivery of SOCS3 reduces the production of inflammatory cytokines and attenuates liver apoptosis and haemorrhagic necrosis (Jo et al., 2005) in mice.

Similar to other members of the SOCS family, SOCS3 contains an N-terminal region, a central SH2 domain and a C-terminal SOCS box (see FIG. 1). The SH2 domain is responsible for direct or competitive inhibition of signalling proteins by interacting with the JAKs or blocking STAT access to docking sites on the receptors (Hilton, 1999; Kile et al., 2002). Although SOCS3 can interact directly with JAK2 via its SH2 domain (Sasaki et al., 2000), the highest-affinity binding sites for the SH2 domain are phosphorylated tyrosines on receptor subunits such as the IL-6 signalling subunit gp130, leptin and EPO receptors (Nicholson et al., 2000; Sasaki et al., 2000; Schmitz et al., 2000; Friederichs et al., 2001).

Extensive mutagenesis experiments involving SOCS3 (Sasaki et al., 1999; Yasukawa et al., 1999) have shown that regions outside the SH2 domain are required for high-affinity binding to phosphorylated tyrosines. These sequences, which extend 12 residues upstream and 40 residues downstream of the SH2 domain, were designated N- and C-ESS (extended SH2 subdomain) regions, respectively. Mutagenesis also identified a 12-residue region upstream of the N-ESS, the Kinase Inhibitory Region (KIR) that was required for kinase inhibition. Over-expression studies have shown that mutations in the SH2 domain and the KIR that abolished SOCS3 interaction with JAK also abrogated inhibition of STAT activity (Sasaki et al., 1999), but it is not clear how important a direct interaction between SOCS3 and JAK2 is in vivo. It is possible that SOCS3 only interacts directly with JAK when bound to sites on JAK-associated receptors such as gp130 (Yoshimura et al., 2005). Whether this then allows interaction with JAKs by the KIR and/or the SH2 domain remains unclear. To date there is no structural information available for any member of the SOCS family to allow an understanding of the molecular mechanism of JAK or STAT inhibition.

There is a need for a greater understanding of the structure of SOCS proteins, such as SOCS3. In particular, a greater appreciation of the structure/functional relationship is required to allow the design of molecules which can be used to modulate SOCS activity.

SUMMARY OF THE INVENTION

The present inventors have determined that the SH2 domain of at least some SOCS proteins are interrupted by an unstructured PEST motif insertion located between two conserved secondary structural elements such that it does not interrupt the function of the domain. This motif has been shown to be an important regulator of protein stability, but can be deleted or mutated without abolishing the biological activity of the SOCS protein.

Thus, in a first aspect the present invention provides a method of increasing the amount of a SOCS protein in a cell, the method comprising administering to the cell a SOCS protein, or polynucleotide encoding therefor, which lacks, or has an inactivated, PEST domain.

In a preferred embodiment, the SOCS protein is SOCS1, SOCS3, SOCS5, SOCS7 or CIS. More preferably, the SOCS protein is SOCS3 or CIS. Even more preferably, the SOCS protein is SOCS3.

The method can be performed on an isolated cell in vitro. However, it is preferred that the method comprises administering to a subject an expression vector encoding said polynucleotide.

Considering the present disclosure, the skilled person can readily produce a SOCS protein, or polynucleotide encoding therefor, which lacks, or has an inactivated, PEST domain, useful for the method of the first aspect. In one embodiment, the SOCS protein which lacks a PEST domain comprises the amino acid sequence as provided in SEQ ID NO:3 or SEQ ID NO:4.

In another aspect, the present invention provides a SOCS protein which lacks a PEST domain, or has an inactivated PEST domain.

Preferably, the protein comprises:
i) an amino acid sequence as provided in SEQ ID NO:3,
ii) an amino acid sequence as provided in SEQ ID NO:4,
iii) an amino acid sequence which is at least 80% identical to i) or ii), or a biologically active fragment of any one of i) to iii).

In one embodiment, the invention provides a fusion protein further comprising at least one other polypeptide sequence.

The at least one other polypeptide may be, for example, a polypeptide that enhances the stability of a polypeptide of the present invention, or a polypeptide that assists in the purification of the fusion protein. In a particularly preferred embodiment, the at least one other polypeptide assists in the fusion protein penetrating a cell.

Also provided is a polynucleotide encoding a SOCS protein of the invention.

For example, the present invention provides an isolated polynucleotide comprising:
i) a nucleotide sequence as provided in SEQ ID NO:15,
ii) a nucleotide sequence as provided in SEQ ID NO:16,
iii) a nucleotide sequence which is at least 80% identical to i) or ii), or portion of any one of i) to iii) encoding a biologically active protein fragment of the invention.

In a further aspect, the present invention provides a vector comprising a polynucleotide of the invention. Preferably, the vector is an expression vector. Such expression vectors typically comprise the polynucleotide encoding the protein being operably linked to a suitable transcription regulatory sequence such as a promoter.

In addition, the invention provides a host cell comprising the protein, the polynucleotide, and/or the vector of the invention.

In a further aspect, the present invention provides a composition comprising the protein, the polynucleotide, and/or the vector of the invention, and an acceptable carrier.

SOCS proteins which lack, or have an inactivated, PEST domain can be used to treat or prevent SOCS related conditions where it is desirable to increase SOCS activity in the subject. Accordingly, in a further aspect, the present invention provides a method of treating or preventing a SOCS related condition in a subject, the method comprising administering to the subject a SOCS protein, or polynucleotide encoding therefor, which lacks, or has an inactivated, PEST domain.

In one embodiment, the SOCS related condition is an inflammatory disease. Preferably, the inflammatory disease is fulminant hepatitis, engraftment syndrome, pulmonary inflammation, acute arthritis and inflammatory bowel disease.

Also provided is the use of a SOCS protein, or polynucleotide encoding therefor, which lacks, or has an inactivated, PEST domain for the manufacture of a medicament for treating or preventing a SOCS related condition.

The present inventors have also determined the three-dimensional structure of SOCS3. This information can be used to identify molecules that act as agonists or antagonists of SOCS activity.

Thus, in a further aspect, the present invention provides a method of identifying a compound which binds SOCS, the method comprising:
i) generating a three-dimensional structure model of
  a) amino acids 22-185, or subset thereof, of SOCS having the atomic coordinates as provided in Table 1, or,
  b) a structure having a root mean square deviation less than about 1.5 Å when superimposed on the corresponding backbone atoms of a), and
ii) designing or screening for a compound which potentially binds the structure.

As the skilled addressee will appreciate, the subset includes a group of amino acids related to the coordinates provided in Table 1 by whole body translations and/or rotations. This group of amino acids may be contiguous and/or be spatially in close proximity.

Preferably, the method further comprises testing the compound designed or screened for in ii) for its ability to bind SOCS. Preferably, the screening is performed using SOCS3, or a biologically active fragment thereof.

In one embodiment, the compound modulates binding of a ligand to SOCS. The ligand can be any molecule known to associate with SOCS in vivo. Examples include, but are not limited to, IL-6 receptor, the leptin receptor and/or the EPO receptor. Preferably, the ligand is the IL-6 receptor, more preferably the gp130 subunit.

Preferably, the SOCS is SOCS1, SOCS2 or SOCS3. More preferably, the SOCS is SOCS3.

Preferably, the compound modulates at least one biological activity of SOCS.

In another embodiment, the method further comprises synthesising the compound which potentially binds the structure.

In an embodiment, the compound binds a region of the SOCS protein which is bound by gp130. Preferably, this region is at least one residue of SOCS3 selected from residues: 53, 54, 71, 94, 104, 127, 164, 165, 166, 167, 168 and 182 of the amino acid sequence provided as SEQ ID NO:1 or SEQ ID NO:2.

In another embodiment, the compound binds to a region of the SOCS protein which is involved in the folding of the protein. Preferably, this region is at least one residue of SOCS3 selected from residues: 34, 38, 41, 70, 80, 175, 176, 177, 178 and 182 of the amino acid sequence provided as SEQ ID NO:1 or SEQ ID NO:2.

In a further embodiment, the compound binds the PEST domain of SOCS. With regard to this embodiment, it is preferred that the method further comprises testing the compound designed or screened for in ii) for its ability to increase the half-life of SOCS.

Preferably, i) and ii) are performed in silico.

In a further embodiment, the method further comprises entering into a computer, through an input device, data comprising the atomic coordinates of the structure.

Preferably, the compound is selected from a real compound, a virtual compound or a combination thereof.

In a further aspect, the present invention provides a computer-based method of identifying a compound which mimics SOCS activity, the method comprising
i) generating a three-dimensional structure model of
  a) amino acids 22-185, or subset thereof, of SOCS having the atomic coordinates as provided in Table 1, or, b) a structure having a root mean square deviation less than about 1.5 Å when superimposed on the corresponding backbone atoms of a), and ii) fitting the structure to that of a candidate compound.

In an embodiment, the compound binds a region of the SOCS protein which is bound by gp130. Preferably, this region is at least one residue of SOCS3 selected from residues: 53, 54, 71, 94, 104, 127, 164, 165, 166, 167, 168 and 182 of the amino acid sequence provided as SEQ ID NO:1 or SEQ ID NO:2.

In another embodiment, the compound binds to a region of the SOCS protein which is involved in the folding of the protein. Preferably, this region is at least one residue of SOCS3 selected from residues: 34, 38, 41, 70, 80, 175, 176, 177, 178 and 182 of the amino acid sequence provided as SEQ ID NO:1 or SEQ ID NO:2.

In a further aspect, the present invention provides a computer system for identifying a compound which binds SOCS, the system containing data representing the structure of a) amino acids 22-185, or subset thereof, of SOCS having the atomic coordinates as provided in Table 1, or, b) a structure having a root mean square deviation less than about 1.5 Å when superimposed on the corresponding backbone atoms of a).

In yet another aspect, the present invention provides a computer for producing a three-dimensional representation of a molecule or molecular complex, wherein the computer comprises:

i) a machine-readable data storage medium comprising a data storage material encoded with machine-readable data, wherein the machine readable data provides the structure of a) amino acids 22-185, or subset thereof, of SOCS having the atomic coordinates as provided in Table 1, or, b) a structure having a root mean square deviation less than about 1.5 Å when superimposed on the corresponding backbone atoms of a), ii) a working memory for storing instructions for processing the machine-readable data;

iii) a central-processing unit coupled to the working memory and to the machine-readable data storage medium, for processing the machine-readable data into the three dimensional representation; and iv) an output hardware coupled to the central processing unit, for receiving the three-dimensional representation.

In another aspect, the present invention provides a computer readable media having recorded thereon coordinate data of a) amino acids 22-185, or subset thereof, of SOCS having the atomic coordinates as provided in Table 1, or, b) a structure having a root mean square deviation less than about 1.5 Å when superimposed on the corresponding backbone atoms of a), In another aspect, the present invention provides a method of treating or preventing a SOCS related condition in a subject, the method comprising administering to the subject a compound identified by the method of the invention.

Preferably, the compound inhibits at least one biological activity of SOCS. Such compounds are useful for treating or preventing a SOCS related condition where it is desirable to reduce the level and/or activity of SOCS. Examples include, but are not limited to, the treatment or prevention of chemotherapy-induced neutropenia, insulin resistance or type-2 diabetes.

In another aspect, the present invention provides a method of mobilising haematopoietic stem cells in a subject, the method comprising administering a compound identified by the method of the invention which inhibits at least one biological activity of SOCS.

The haematopoietic stem cells can be, but are not limited to, granulocyte-macrophage progenitors, erythroid progenitors and megakaryocyte progenitors.

In a further aspect, the present invention provides a method of reducing the appetite of a subject, the method comprising administering a compound identified by the method of the invention which inhibits at least one biological activity of SOCS.

Also provided is a compound identified using a method of the invention, as well as a pharmaceutical composition comprising said compound.

As will be apparent, preferred features and characteristics of one aspect of the invention are applicable to many other aspects of the invention.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The invention is hereinafter described by way of the following non-limiting Examples and with reference to the accompanying figures.

BRIEF DESCRIPTION OF THE ACCOMPANYING DRAWINGS

FIG. 1. Domain architecture and sequence homology of SOCS3. The domain architecture of SOCS3 is shown as a schematic diagram. SOCS3 consists of 225 amino acids, with a small N-terminal domain, kinase inhibitory region, extended SH2 sub-domain, SH2 domain and C-terminal SOCS box. As described herein, the extended SH2 domain of SOCS3 extends from residue 44-185 and is interrupted by a 35 amino acid PEST motif. The present inventors have determined the structure of SOCS3 from residues 22-185. The sequence homology of this region across mammalian, avian and xenopus SOCS3 is shown aligned to mouse SOCS3. Sequence identity is indicated above each residue, as are the secondary structural elements using standard SH2 domain nomenclature. Mutations affecting kinase inhibition or SH2 domain function are shown as asterisks. (Murine SOCS3=SEQ ID NO: 12; rat SOCS=SEQ ID NO: 5; human SOCS=SEQ ID NO: 13; canine SOCS=SEQ ID NO: 6; bovine SOCS=SEQ ID NO: 7; chick SOCS=SEQ ID NO: 8; xenopus SOCS=SEQ ID NO: 9)

Figure 2:
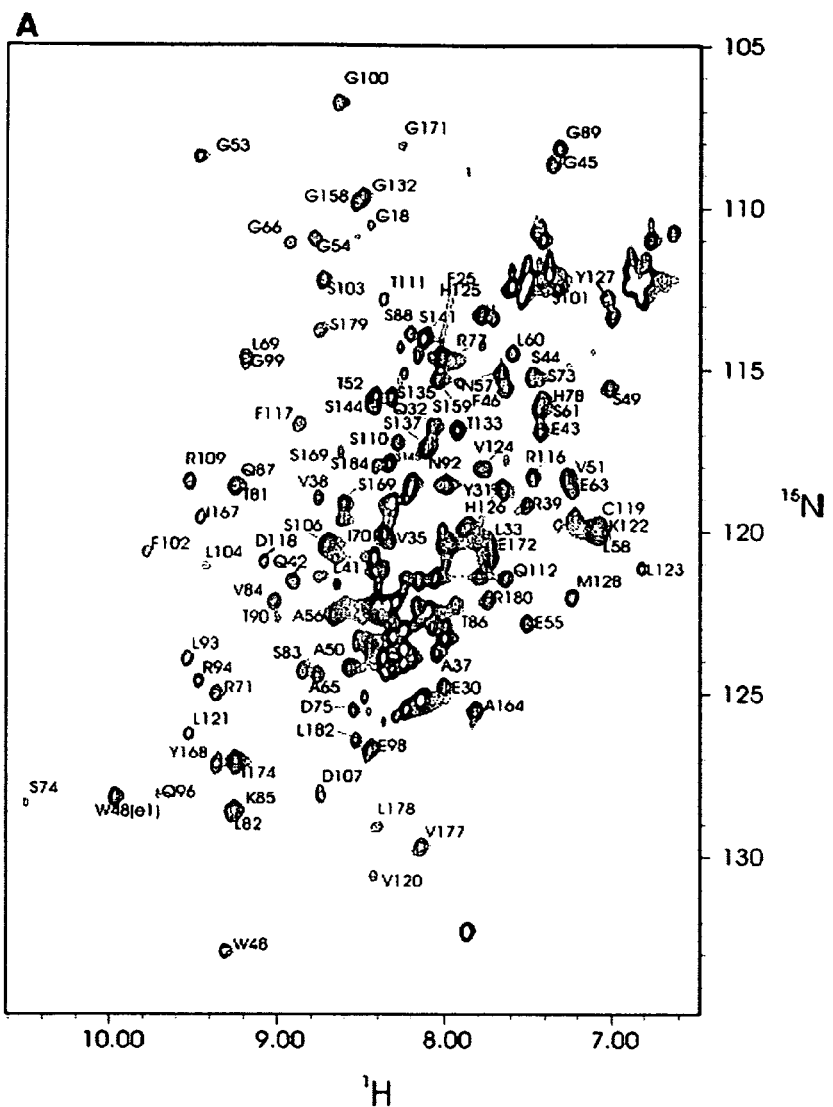
Figure 2:
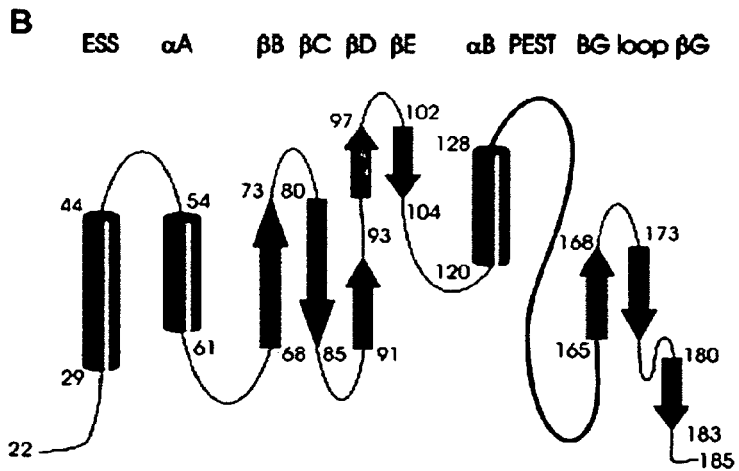

FIG. 2. $^{15}N$-$^{1}H$ HSQC spectrum and secondary structure assignment of SOCS3(22-185).

(A) The $^{15}N$-$^{1}H$ HSQC spectrum is shown of 0.1 mM SOCS3 at 500 MHz and 298 K in 50 mM sodium-phosphate buffer (pH 6.7) containing 2 mM dithiothreitol. The assigned residues are labelled with their residue number in the HSQC; some assignment labels are omitted for clarity.

(B) The secondary structure of SOCS3 was assigned by examining NOE patterns, analyses of backbone and $^{13}C_\beta$ chemical shifts, and TALOS predictions (Waksman et al., 1993), and is shown schematically with residue numbers marking the boundaries of each motif. The PEST motif is shown as a thick black line. The relevant secondary structure motifs are indicated at the top of the figure with the nomenclature used by Grucza et al. (1999). The topology of the β-sheet and two β-hairpins was determined by examining long-range backbone-backbone NOEs. ESS, extended SH2 subdomain; PEST, PEST motif.

Figures 3, 4:
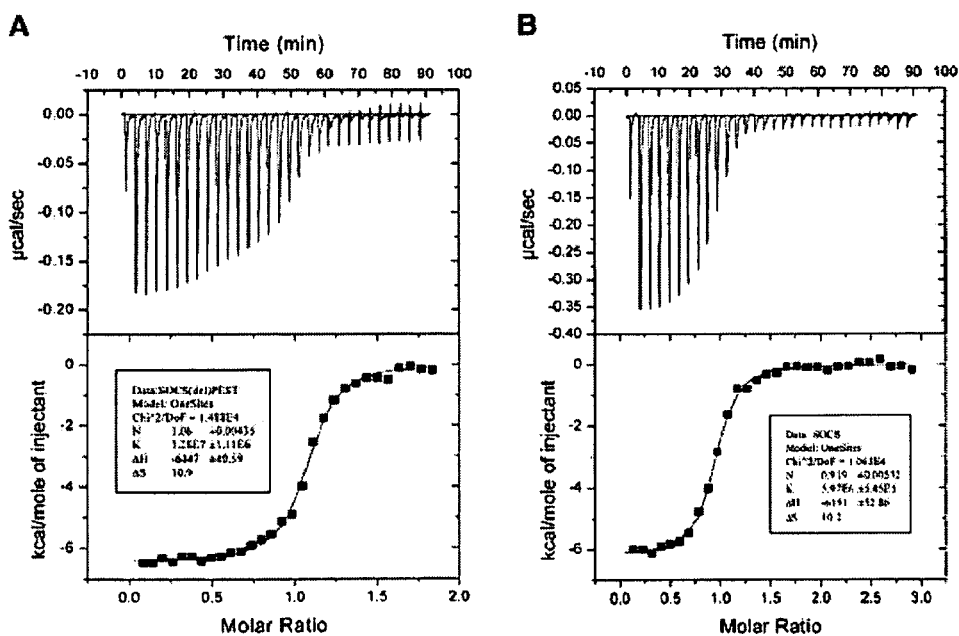

FIG. 3. PEST sequence conservation in SOCS3. Sequence alignment of the region of SOCS3 containing the PEST motif for a number of mammalian species is shown, with conserved residues in the unstructured PEST motif highlighted. The numbering refers to mouse SOCS3. The unstructured residues defined by this study are shown in bold. (Murine SOCS3=SEQ ID NO: 18; rat SOCS=SEQ ID NO: 19; human SOCS=SEQ ID NO: 20; canine SOCS=SEQ ID NO: 21; bovine SOCS=SEQ ID NO: 22)

FIG. 4. SOCS3 lacking the PEST motif binds a gp130 peptide with high affinity.

(A) Titration of 80 μM gp130 peptide into 10 μM SOCS3 (Δ101-133). The integrated heats from which the heat of dilution has been subtracted are shown, as well as the fit to a single site binding isotherm that yielded $K_d$ 78 nM and $\Delta H$ −6.4 kcal mol$^{-1}$.

(B) Titration of 160 μM gp130 peptide into 13 μM wild type SOCS3. The fit to a single site binding isotherm is shown, yielding a $K_d$ of 168 nM and a $\Delta H$ of −6.2 kcal.mol$^{-1}$. Both the wild-type and (Δ101-133) proteins used spanned residues 22-185 and not 22-225 because of the higher solubility of the former.

Figure 5:
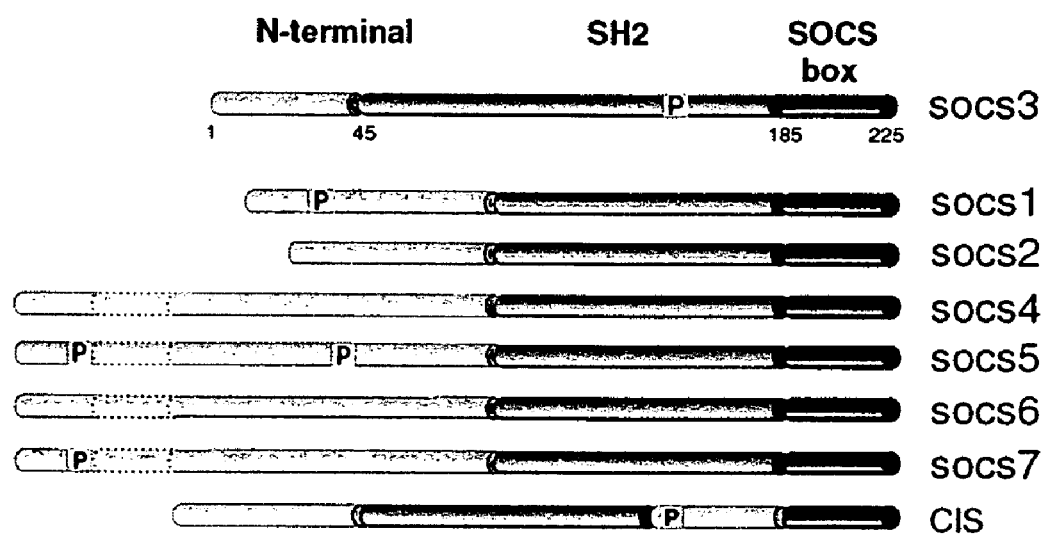

FIG. 5. The suppressor of cytokine signalling (SOCS) family of proteins. The eight members of the SOCS family [SOCS1-7 and cytokine-inducible SH2-containing protein (CIS)] are shown schematically. All eight members of the SOCS family contain a C-terminal SOCS box, a central SH2 domain and an N-terminal domain of varying lengths. SOCS3 and CIS also contain a small insertion of ≈60 residues between the SH2 domain and the SOCS box. The SH2 domain boundaries shown for SOCS3 are as identified in this study. The position of potential PEST motifs in the SOCS family, as suggested by this work, are indicated by a boxed 'P'; note that they are not shown to scale. SOCS4-7 have much longer N-terminal domains than the other SOCS family members (300-400 residues), the dotted lines indicate that these regions are not drawn to scale. The residue numbering refers to SOCS3 only.

Figure 6:
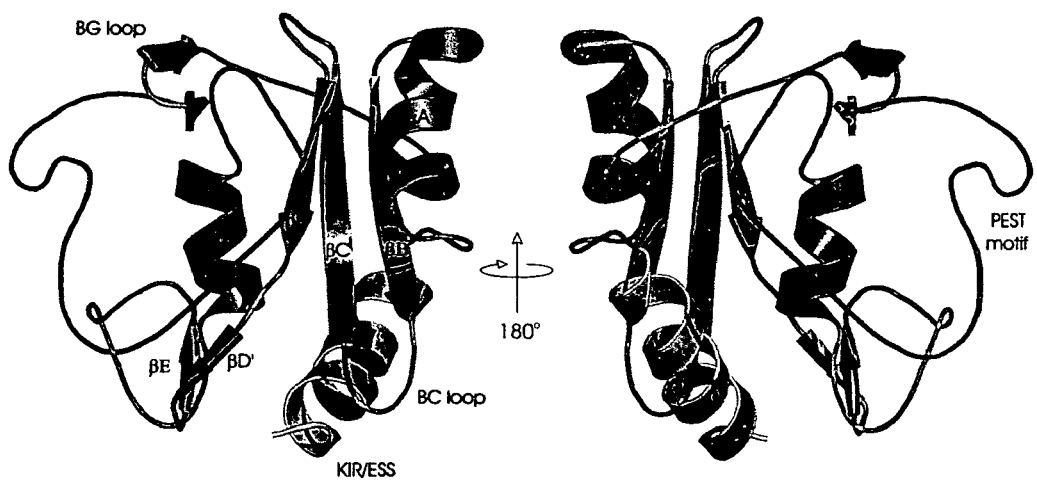
Figure 6:
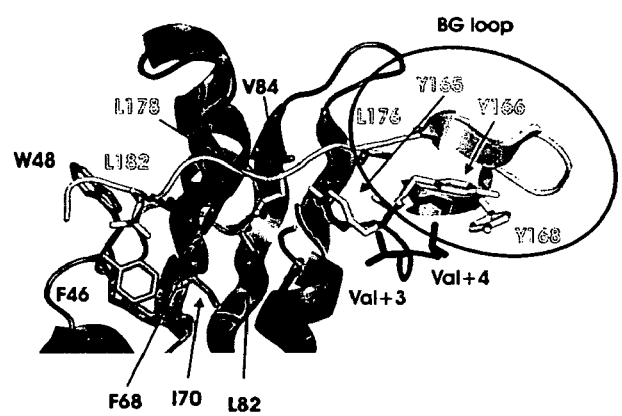

FIG. 6. Structure of murine SOCS3.

(A) Two views of a ribbon diagram of murine SOCS3, from Glu30-Asn185, with the secondary structural elements highlighted. The first half of the KIR is omitted as it is unstructured.

(B) The residues downstream of the PEST motif form structurally and functionally significant regions of the SH2 domain. This region of SOCS3 (residues 164-185) makes a number of important hydrophobic contacts both with the core of the SH2 domain as well as residues in the pTyr-peptide. Residues 164-176 form the BG loop (circled) that directly interacts with the gp130 pTyr-peptide. Residues involved in direct contacts are shown with their side chains displayed in "stick" representation. The view shown in B is approximately the same as that shown on the right-hand side of A.

Figure 7:
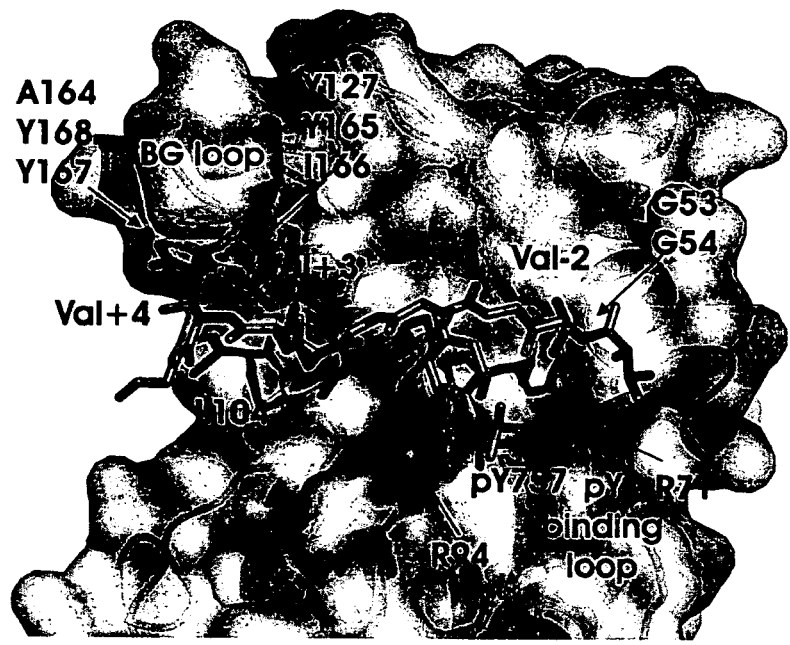
Figure 7:
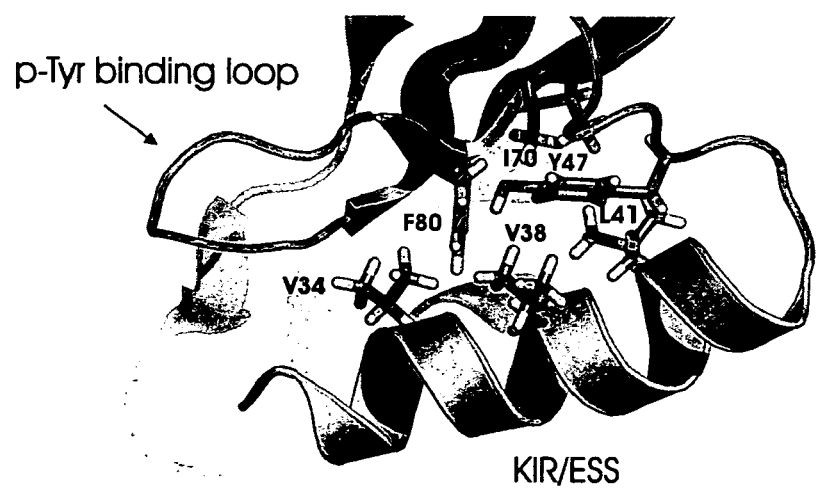

FIG. 7. Interactions between the SH2 domain, pTyr-peptide and extended SH2 subdomain.

(A) The molecular surface of SOCS3 (transparent white) is shown complexed with the gp130 peptide (stick representation) with important residues labelled. The regions of the SH2 domain involved in binding are indicated with single letter amino-acid code and colored yellow (hydrophobic residues) or blue (positively charged residues). The important pTyr binding loop and BG loop are indicated. Valine residues in the pTyr peptide located both downstream and upstream of the pTyr are involved in hydrophobic interactions with the SH2 domain and are indicated with 3-letter amino-acid codes. Whilst the exact geometry of the pTyr is not restrained in our structure because of a lack of NOEs, it is situated near a positively-charged patch on the surface of the domain formed by Arg71 and 94.

(B) Residues in the ESS help determine the geometry of the pTyr binding pocket. A view of SOCS3 showing that residues from the Extended SH2 subdomain (ESS), in particular Val34, Ala37, Val38 and Leu41, interact with residues adjacent to the pTyr binding loop (BC loop), Ile70 and Phe80. Tyr47 is also involved in mediating contacts between the N-ESS and BC loop.

Figure 8:
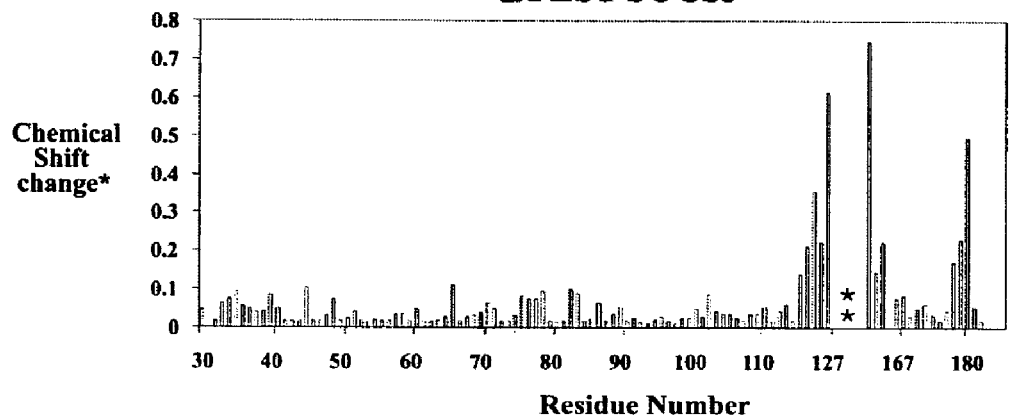
Figure 8:
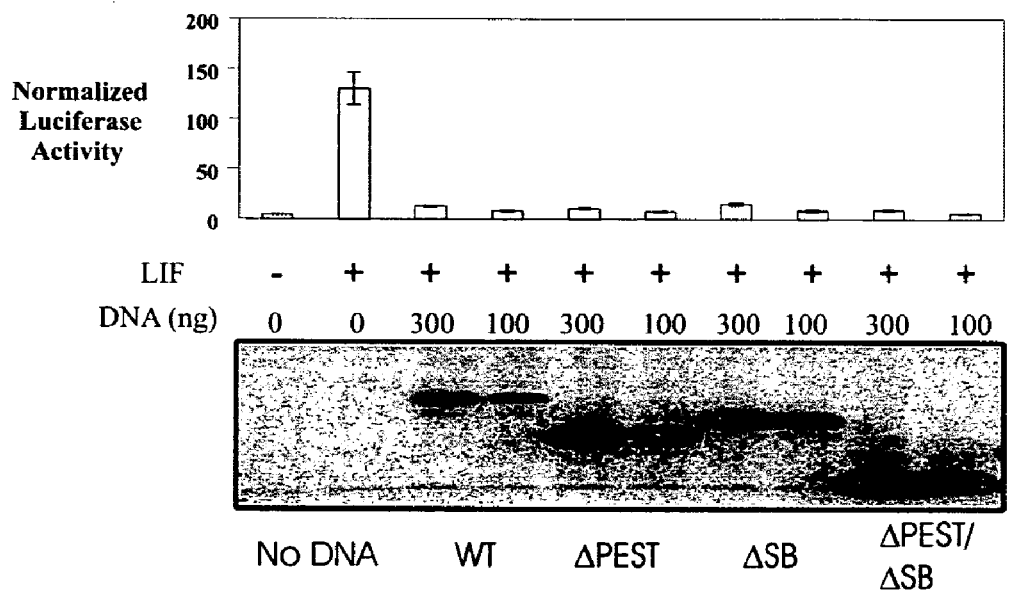

FIG. 8. Removing the PEST motif does not affect the structure or function of SOCS3.

(A) The structure of SOCS3 is not significantly affected by removing the PEST motif. Backbone amide chemical shift differences between residues in wild-type SOCS3 and ΔPEST SOCS3, which has residues 129-163 replaced by GSGSGSGS (SEQ ID NO:10), are plotted against residue number; amide proton and nitrogen chemical shift differences were averaged according to Δδav, a weighted average of the $^{15}$N and $^{1}$HN chemical shifts as follows: $\Delta\delta av=\{0.5[\Delta\delta(^1HN)^2+(0.2\Delta\delta(15N))^2]\}^{1/2}$ (Pellecchia et al., 1999). The position of the PEST sequence is marked by a double asterisk.

(B) SOCS3 PEST deletion mutants are able to inhibit STAT activation. 293T cells were transiently transfected with 100 or 300 ng cDNA expressing various Flag-tagged SOCS-3 proteins in the presence of the Stat3-responsive reporter gene. The SOCS3 constructs expressed either wild-type SOCS3 (WT), SOCS3 lacking the PEST sequence (ΔPEST), the SOCS box (ΔSB) or both the SOCS box and PEST sequence (ΔPEST/ΔSB). Cells were incubated in the presence (+) or absence (−) of 10 ng/ml LIF overnight and cell extracts prepared. Upper panel: Luciferase activity from triplicate samples was determined and normalized against *Renilla luciferase* activity. Lower panel: Lysates were analysed by Western blot with anti-Flag antibody.

Figure 9:
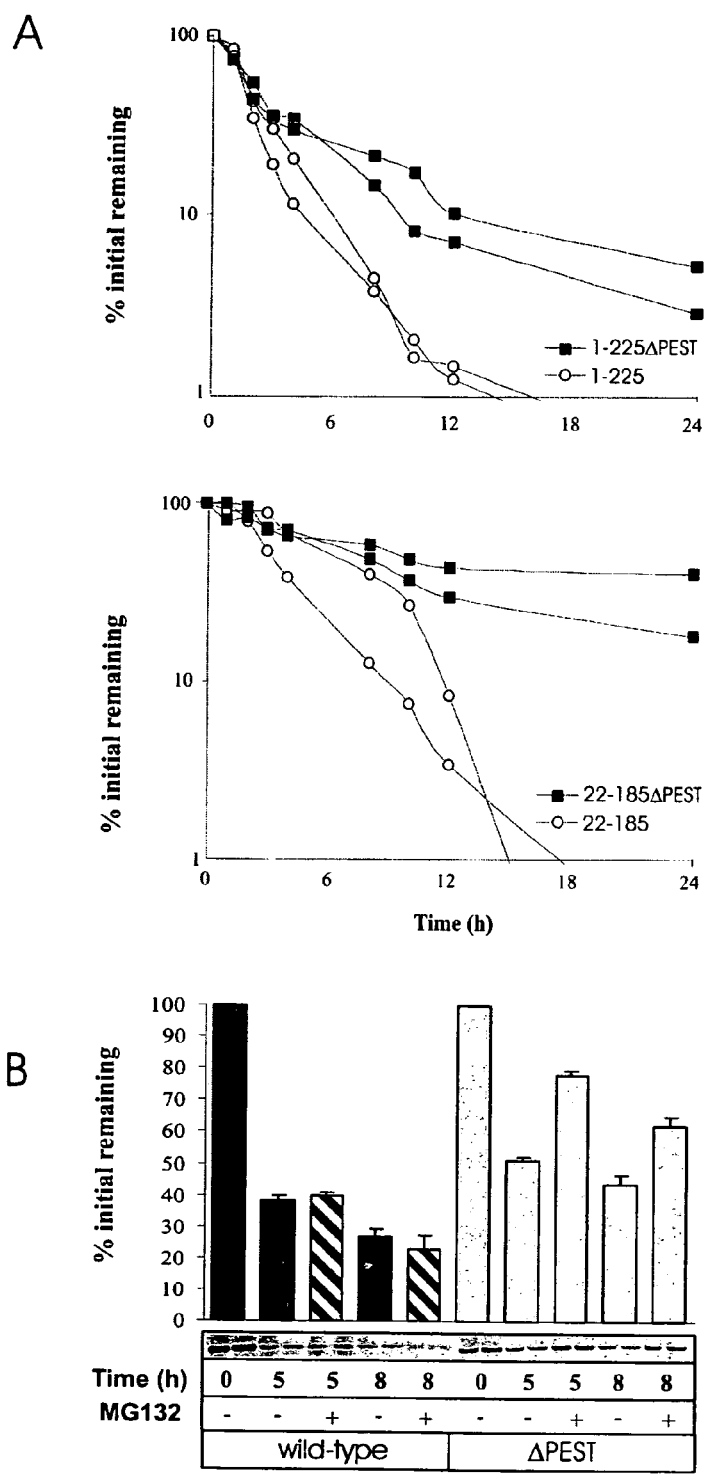

FIG. 9. Removing the PEST motif improves the intracellular half-life of SOCS3 and affects its degradation mechanism.

(A) Duplicate pulse chase experiments in 293T cells performed after transfection of (upper panel) wild-type (1-225) or ΔPEST (Δ129-163) SOCS3 DNA and (lower panel) ΔNC-SOCS3 (22-185) or ΔNC-Δ129-163 (22-185 ΔPEST) SOCS3 DNA. The amount of labelled protein remaining is shown as a perceintage of initial levels and plotted as a semi-log graph. Removing the PEST motif improved its in vivo stability in both a wild-type and ΔNC background which lacks the N-terminal domain and C-terminal SOCS box. Duplicate experiments are shown in each panel (B) Removing the PEST motif alters the intracellular degradation pathway of SOCS3. Pulse chase experiments were performed on 293T cells transfected with wild-type SOCS3 (black) or ΔPEST SOCS3 (grey) and incubated in the presence (hashed bars) and absence (solid bars) of MG-132, a proteasome inhibitor. Experiments were performed in duplicate according to the protocol in (A) but with the addition of 10 μM MG-132 and the protein levels monitored over eight hours. The presence of MG-132, a proteasome inhibitor, had no effect on the half-life of wild-type SOCS3 but significantly increased the half-life of SOCS3 when the PEST motif was deleted.

KEY TO THE SEQUENCE LISTING

SEQ ID NO: 1—Murine SOCS-3.
SEQ ID NO: 2—Human SOCS-3.
SEQ ID NO: 3—ΔPEST SOCS-3$_{(22-185)}$.
SEQ ID NO: 4—ΔPEST SOCS-3$_{(22-225)}$.
SEQ ID NO: 5—Rat partial SOCS-3.
SEQ ID NO: 6—Canine partial SOCS-3.
SEQ ID NO: 7—Bovine partial SOCS-3.
SEQ ID NO: 8—Chicken partial SOCS-3.
SEQ ID NO: 9—Xenopus partial SOCS-3.
SEQ ID NO: 10—PEST replacement fragment.
SEQ ID NO: 11—Phosphotyrosine peptide gp130.
SEQ ID NO: 12—Murine partial SOCS-3.
SEQ ID NO: 13—Human partial SOCS-3.
SEQ ID NO: 14—Flag tag.
SEQ ID NO: 15—Nucleotide sequence encoding ΔPEST SOCS-3$_{(22-185)}$.
SEQ ID NO: 16—Nucleotide sequence encoding ΔPEST SOCS-3$_{(22-225)}$.
SEQ ID NO: 17—Cell-penetrating motif.
SEQ ID NO:18—PEST domain of murine SOCS3.
SEQ ID NO:19—PEST domain of rat SOCS3.
SEQ ID NO:20—PEST domain of human SOCS3.
SEQ ID NO:21—PEST domain of canine SOCS3.
SEQ ID NO:22—PEST domain of bovine SOCS3.

DETAILED DESCRIPTION OF THE INVENTION

General Techniques and Definitions

Unless specifically defined otherwise, all technical and scientific terms used herein shall be taken to have the same meaning as commonly understood by one of ordinary skill in the art (e.g., in cell culture, molecular genetics, structural biology, immunology, immunohistochemistry, protein chemistry, and biochemistry).

Unless otherwise indicated, the recombinant protein, cell culture, and immunological techniques utilized in the present invention are standard procedures, well known to those skilled in the art. Such techniques are described and explained throughout the literature in sources such as, J. Perbal, A Practical Guide to Molecular Cloning, John Wiley and Sons (1984), J. Sambrook et al., Molecular Cloning: A Laboratory Manual, Cold Spring Harbour Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), and F. M. Ausubel et al. (editors), Current Protocols in Molecular Biology, Greene Pub. Associates and Wiley-Interscience (1988, including all updates until present), Ed Harlow and David Lane (editors) Antibodies: A Laboratory Manual, Cold Spring Harbour Laboratory, (1988), and J. E. Coligan et al. (editors) Current Protocols in Immunology, John Wiley & Sons (including all updates until present), and are incorporated herein by reference.

As used herein, the terms "SOCS" and a "SOCS protein" generally refers to any member of the "suppressor of cytokine signalling" family (Alexander and Hilton, 2004). In particular, a SOCS protein of the invention is any one of SOCS 1 to 7, and the cytokine-inducible SH-2 containing protein (CIS). These proteins are characterized by an N-terminal region of varying size, a central SH2 domain and a C-terminal SOCS box (see FIG. 5). In a preferred embodiment, the SOCS protein is SOCS1, SOCS2 or SOCS3. In a particularly preferred embodiment, the SOCS protein comprises a SH2 domain and a C-terminal SOCS box (see FIG. 5). In a preferred embodiment, the SOCS protein is SOCS3.

A used herein, the term "biological activity of SOCS" refers to any function of a SOCS protein in vivo. With regard to SOCS3, a biological activity includes, but is not limited to, the ability to inhibit LIF-induced Stat3 activity.

As used herein, a "PEST domain" or "PEST motif" refers to a region of a SOCS protein having a high concentration of proline, glutamic acid, serine and/or threonine residues. PESTs typically begin and end with positively charged residues, and have no internal lysine, arginine or histidine residues. As the skilled addressee will appreciate, PEST domains are known in other types of proteins. PEST domains can be identified by eye, or by using a computer program such as www.at.embnet.org/embnet/tools/bio/PESTfind (Rechsteiner and Rogers, 1996).

As used herein, a SOCS protein with an inactivated PEST domain means that the native PEST domain of the protein has been mutated/modified such that the stability (half-life) of the resulting protein is increased when compared to the native SOCS protein.

As used herein, a "SOCS related condition" is any disease of a subject that may benefit from the levels and/or activity of a SOCS protein being modulated. In one embodiment, it is desirable to reduce SOCS level/activity, for example in the treatment or prevention of chemotherapy-induced neutropenia, insulin resistance or type-2 diabetes. In another embodiment, it is desirable to increase SOCS level/activity, for example in the treatment or prevention of an inflammatory disease.

As used herein, the phrase "root mean square deviation" ("RMS") means the square root of the arithmetic mean of the squares of the deviations from the mean and denotes a measure of the structural relationship between two or more species of proteins. It may be determined by, for example, superimposing one three-dimensional structure onto another, which may be solved by using, for example, X-ray crystallography or nuclear magnetic resonance (NMR), and then, calculating the difference in the RMS of the distance from the Cα and/or backbone (N, C, O, and Cα) trace (or atoms) of one protein to another protein in units of Angstroms (Å). The superimposition of three-dimensional structures may be performed using a molecular modeling program such as, for example, the Superimpose command in Insight II (Accelrys Inc., San Diego, Calif.), CNX (Accelrys Inc., San Diego, Calif.), XtalView™ (Scripps Research Institute, La Jolla, Calif.), SYBYL™ (Tripos, Inc., St. Louis, Mo.), or O (Aarhus Univ., Denmark (Jones et al., 1991)), or other related computer modeling programs or scripts, alone or in combination. For example, the Superimpose command in Insight II, performs a minimum RMS alignment of two molecules on selected sets of atoms from each molecule is then outputs the RMS deviation value between the selected atoms of the superimposed molecules. The closer the relationship between the three-dimensional structures, the smaller the RMS deviation value.

By "stereochemical complementarity" we mean that the compound or a portion thereof makes a sufficient number of energetically favourable contacts with the SOCS protein, or topographical region thereof, as to have a net reduction of free energy on binding to the SOCS protein, or topographical region thereof.

A "mimetic" of a compound refers to a compound in which chemical structures of the compound, in this case a SOCS protein, that are necessary for functional activity have been replaced with other chemical structures which mimic the conformation of the compound or peptides thereof. The term "mimetic" as used herein is also intended to include molecules which mimic the chemical structure of a L or D-peptidic structure, and retain the functional properties of a L- or D-peptidic structure.

"Operably linked" as used herein refers to a functional relationship between two or more nucleic acid (e.g., DNA) segments. Typically, it refers to the functional relationship of transcriptional regulatory element (promoter) to a transcribed sequence. For example, a promoter is operably linked to a coding sequence, such as a polynucleotide defined herein, if it stimulates or modulates the transcription of the coding sequence in an appropriate cell. Generally, promoter transcriptional regulatory elements that are operably linked to a transcribed sequence are physically contiguous to the transcribed sequence, i.e., they are cis-acting. However, some transcriptional regulatory elements, such as enhancers, need not be physically contiguous or located in close proximity to the coding sequences whose transcription they enhance.

As used herein, the term "gene" is to be taken in its broadest context and includes the deoxyribonucleotide sequences comprising the protein coding region of a structural gene and including sequences located adjacent to the coding region on both the 5' and 3' ends for a distance of at least about 2 kb on either end. The sequences which are located 5' of the coding region and which are present on the MRNA are referred to as 5' non-translated sequences. The sequences which are located 3' or downstream of the coding region and which are present on the mRNA are referred to as 3' non-translated sequences. The term "gene" encompasses both cDNA and genomic forms of a gene. A genomic form or clone of a gene contains the coding region which may be interrupted with non-coding sequences termed "introns" or "intervening regions" or "intervening sequences." Introns are segments of a gene which are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide. The term "gene" includes a synthetic or fusion molecule encoding all or part of the proteins of the invention described herein and a complementary nucleotide sequence to any one of the above.

Protein-Structure Based Design of Agonists and Antagonists

For a compound to bind a SOCS protein, it will typically require a suitable level of stereochemical complementarity. In general, the design of a molecule possessing stereochemical complementarity can be accomplished by means of techniques that optimize, chemically and/or geometrically, the "fit" between a molecule and a target receptor. Known techniques of this sort are reviewed by Sheridan and Venkataraghavan, 1987; Goodford, 1984; Beddell, 1985; Hol, 1986; Verlinde and Hol, 1984; Walters et al., 1998; Langer and Hoffmann, 2001; Good, 2001; Gane and Dean, 2000.

There are at least two approaches to designing a molecule, according to the present invention, that complements the stereochemistry of a SOCS protein. The first approach is to in silico directly dock molecules from a three-dimensional structural database, to the receptor site, using mostly, but not exclusively, geometric criteria to assess the goodness-of-fit of a particular molecule to the site. In this approach, the number of internal degrees of freedom (and the corresponding local minima in the molecular conformation space) is reduced by considering only the geometric (hard-sphere) interactions of two rigid bodies, where one body (the active site) contains "pockets" or "grooves" that form binding sites for the second body (the complementing molecule, as ligand).

This approach is illustrated by Kuntz et al. (1982) and Ewing et al. (2001), whose algorithm for ligand design is implemented in a commercial software package, DOCK version 4.0, distributed by the Regents of the University of California and further described in a document, provided by the distributor, which is entitled "Overview of the DOCK program suite" the contents of which are hereby incorporated by reference. Pursuant to the Kuntz algorithm, the shape of a region of interest (binding site) is defined as a series of overlapping spheres of different radii. For example, mapped by structural data of SOCS3 bound to gp130 as shown in Table 1. One or more extant databases of crystallographic data, such as the Cambridge Structural Database System maintained by Cambridge University (University Chemical Laboratory, Lensfield Road, Cambridge CB2 1EW, U.K.), the Protein Data Bank maintained by the Research Collaboratory for Structural Bioinformatics (Rutgers University, N.J., U.S.A.), LeadQuest (Tripos Associates, Inc., St. Louis, Mo.), Available Chemicals Directory (Molecular Design Ltd., San Leandro, Calif.), and the NCI database (National Cancer Institute, U.S.A) is then searched for molecules which approximate the shape thus defined.

Molecules identified in this way, on the basis of geometric parameters, can then be modified to satisfy criteria associated with chemical complementarity, such as hydrogen bonding, ionic interactions and Van der Waals interactions. Different scoring functions can be employed to rank and select the best molecule from a database (see, for example, Bohm and Stahl, 1999). The software package FlexX, marketed by Tripos Associates, Inc. (St. Louis, Mo.) is another program that can be used in this direct docking approach (Rarey et al., 1996).

The second preferred approach entails an assessment of the interaction of respective chemical groups ("probes") with the active site at sample positions within and around the site, resulting in an array of energy values from which three-dimensional contour surfaces at selected energy levels can be generated. The chemical-probe approach to ligand design is described, for example, by Goodford, (1985), and is implemented in several commercial software packages, such as GRID (product of Molecular Discovery Ltd., West Way House, Elms Parade, Oxford OX2 9LL, U.K.). Pursuant to this approach, the chemical prerequisites for a site-complementing molecule are identified at the outset, by probing the active site with different chemical probes, e.g., water, a methyl group, an amine nitrogen, a carboxyl oxygen, and a hydroxyl. Favoured sites for interaction between the active site and each probe are thus determined, and from the resulting three-dimensional pattern of such sites a putative complementary molecule can be generated. This may be done either by programs that can search three-dimensional databases to identify molecules incorporating desired pharmacophore patterns or by programs which using the favoured sites and probes as input perform de novo design.

Programs suitable for searching three-dimensional databases to identify molecules bearing a desired pharmacophore include: MACCS-3D and ISIS/3D (Molecular Design Ltd., San Leandro, Calif.), ChemDBS-3D (Chemical Design Ltd., Oxford, U.K.), and Sybyl/3DB Unity (Tripos Associates, Inc., St. Louis, Mo.).

Programs suitable for pharmacophore selection and design include: DISCO (Abbott Laboratories, Abbott Park, Ill.), Catalyst (Accelrys, San Diego, Calif.), and ChemDBS-3D (Chemical Design Ltd., Oxford, U.K.).

Databases of chemical structures are available from a number of sources including Cambridge Crystallographic Data Centre (Cambridge, U.K.), Molecular Design, Ltd., (San Leandro, Calif.), Tripos Associates, Inc. (St. Louis, Mo.), and Chemical Abstracts Service (Columbus, Ohio).

De novo design programs include Ludi (Biosym Technologies Inc., San Diego, Calif.), Leapfrog (Tripos Associates, Inc.), Aladdin (Daylight Chemical Information Systems, Irvine, Calif.), and LigBuilder (Peking University, China).

Mimetics, such as peptido- and organomimetics can be designed to fit, e.g., a peptide binding site with current computer modeling software (using computer assisted drug design or CADD) (Walters, 1993; Munson, 1995). Also included within the scope of the disclosure are mimetics prepared using such techniques. In one example, a mimetic mimics a peptide or region of SOCS-3.

Mimetics can be generated using software that can derive a virtual peptide model from several peptide structures. This can be done using the software derived from SLATE algorithm (Perkin et al., 1995; Mills et al., 2001; De Esch et al., 2001; Mills et al., 1997). One example of the program derived from SLATE algorithm is Quasi by De Novo Pharmaceutical. This program superimposes several active but apparently dissimilar peptide molecules to arrive at the most probable structures essential for activity (with minimum energy constraint). This can be used to generate a mold or target binding site with predicted position of hydrogen binding atoms in three dimensional space. This can then be used to generate a non-peptide mimic of the original ligand peptides. These molecule generator softwares are now commercially available (example Skelgen and Skelgen II).

Other approaches to designing peptide analogs, derivatives and mimetics are also well known in the art, see for example Farmer, 1980; Ball and Alewood, 1990; Morgan and Gainor, 1989; Freidinger, 1989; Sawyer, 1995; Smith et al., 1995; Smith et al., 1994; and Hirschman et al., 1993.

The invention may be implemented in hardware or software, or a combination of both. However, preferably, the invention is implemented in computer programs executed on programmable computers each comprising a processor, a data storage system (including volatile and non-volatile memory and/or storage elements), at least one input device, and at least one output device. Program code is applied to input data to perform the functions described above and generate output information. The output information is applied to one or more output devices, in known fashion. The computer may be, for example, a personal computer, microcomputer, or workstation of conventional design.

Each program is preferably implemented in a high level procedural or object-oriented programming language to communicate with a computer system. However, the programs can be implemented in assembly or machine language, if desired. In any case, the language may be compiled or interpreted language.

Each such computer program is preferably stored on a storage medium or device (e.g., ROM or magnetic diskette) readable by a general or special purpose programmable computer, for configuring and operating the computer when the storage media or device is read by the computer to perform the procedures described herein. The inventive system may also be considered to be implemented as a computer-readable storage medium, configured with a computer program, where the storage medium so configured causes a computer to operate in a specific and predefined manner to perform the functions described herein.

If required, the prospective drug (agonist or antagonist) can be synthesized or obtained from a suitable source such as a commercial supplier. It can then be placed into any standard binding assay to test its effect on the ability to bind a SOCS protein, and/or placed in a standard assay to determine its ability to modulate the biological activity of a SOCS protein.

For all of the drug screening assays described herein further refinements to the structure of the drug will generally be necessary and can be made by the successive iterations of any and/or all of the steps provided by the particular drug screening assay.

Agonists and Antagonists

As outlined above, the structural information provided herein can be employed in a screening processes for compounds which mimic (agonists) or inhibit (antagonists) SOCS activity.

Examples of potential antagonists include antibodies, oligosaccharides and derivatives thereof, or in some cases peptides which bind to, for example, the gp130 binding domain of SOCS3. Antagonists may also disrupt the normal folding of the SOCS protein which in turn will typically inhibit the biological ability of the protein.

A potential antagonist is a small molecule which binds to the gp130 binding domain of SOCS3, making it inaccessible to the receptor. Examples of small molecules include, but are not limited to, small peptides or peptide-like molecules. The small molecules may mimic the structure of the SOCS3 gp130 binding domain, preventing the protein from associating with gp130.

Gene Therapy

The polynucleotides, polypeptides, agonists and antagonists that are polypeptides described herein, and/or identified using the methods described herein, may be employed in accordance with the present invention by expression of such polypeptides in treatment modalities often referred to as "gene therapy". In particular, a SOCS protein which lacks, or has an inactivated, PEST domain is more stable than native SOCS but still able to, for example, inhibit LIF-induced Stat3 activity can be employed in gene therapy techniques for the treatment of disease. Thus, for example, cells from a patient may be engineered with a polynucleotide, such as a DNA or RNA, to encode a polypeptide ex vivo. The engineered cells can then be provided to a patient to be treated with the polypeptide. In this embodiment, cells may be engineered ex vivo, for example, by the use of a retroviral plasmid vector containing RNA encoding a polypeptide of the present invention which can be used to transform stem cells or differentiated stem cells. Such methods are well-known in the art and their use in the present invention will be apparent from the teachings herein.

Further, cells may be engineered in vivo for expression of a polypeptide in vivo by procedures known in the art. For example, a polynucleotide encoding a SOCS protein which lacks, or has an inactivated, PEST domain may be engineered for expression in a replication defective retroviral vector or adenoviral vector or other vector (e.g., poxvirus vectors). The expression construct may then be isolated. A packaging cell is transduced with a plasmid vector containing RNA encoding a SOCS protein which lacks, or has an inactivated, PEST domain, such that the packaging cell now produces infectious viral particles containing the gene of interest. These producer cells may be administered to a patient for engineering cells in vivo and expression of the polypeptide in vivo. These and other methods for administering a polypeptide of the present invention should be apparent to those skilled in the art from the teachings of the present invention.

Retroviruses from which the retroviral plasmid vectors hereinabove-mentioned may be derived include, but are not limited to, Moloney Murine Leukemia Virus, Spleen Necrosis Virus, Rous Sarcoma Virus, Harvey Sarcoma Virus, Avian Leukosis Virus, Gibbon Ape Leukemia Virus, Human Immunodeficiency Virus, Adenovirus, Myeloproliferative Sarcoma Virus, and Mammary Tumor Virus. In a preferred embodiment, the retroviral plasmid vector is derived from Moloney Murine Leukemia Virus.

Such vectors will include one or more promoters for expressing the polypeptide. Suitable promoters which may be employed include, but are not limited to, the retroviral LTR; the SV40 promoter; and the human cytomegalovirus (CMV) promoter. Cellular promoters such as eukaryotic cellular promoters including, but not limited to, the histone, RNA polymerase III, and β-actin promoters, can also be used. Additional viral promoters which may be employed include, but are not limited to, adenovirus promoters, thymidine kinase (TK) promoters, and B19 parvovirus promoters. The selection of a suitable promoter will be apparent to those skilled in the art from the teachings contained herein.

The nucleic acid sequence encoding a SOCS protein which lacks, or has an inactivated, PEST domain will be placed under the control of a suitable promoter. Suitable promoters which may be employed include, but are not limited to, adenoviral promoters, such as the adenoviral major late promoter; or heterologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs (including the modified retroviral LTRs herein above described); the β-actin promoter; and human growth hormone promoters. Preferably, the promoter drives expression of the gene in a cell which naturally produces SOCS. The promoter may also be the native promoter which controls the gene encoding the polypeptide.

The retroviral plasmid vector is employed to transduce packaging cell lines to form producer cell lines. Examples of packaging cells which may be transfected include, but are not limited to, the PE501, PA317, Ψ-2, Ψ-AM, PA12, T19-14X, VT-19-17-H2, YCRE, YCRIP, GP+E-86, GP+envAm12, and DAN cell lines as described by Miller (1990). The vector may be transduced into the packaging cells through any means known in the art. Such means include, but are not limited to, electroporation, the use of liposomes, and CaPO$_4$ precipitation. In one alternative, the retroviral plasmid vector may be encapsulated into a liposome, or coupled to a lipid, and then administered to a host.

The producer cell line will generate infectious retroviral vector particles, which include the nucleic acid sequence(s) encoding a SOCS protein which lacks, or has an inactivated, PEST domain. Such retroviral vector particles may then be employed to transduce eukaryotic cells, either in vitro or in vivo. The transduced eukaryotic cells will express the nucleic acid sequence(s) encoding the polypeptide. Eukaryotic cells which may be transduced include, but are not limited to, embryonic stem cells, embryonic carcinoma cells, as well as hematopoietic stem cells, hepatocytes, fibroblasts, myoblasts, keratinocytes, endothelial cells, and bronchial epithelial cells.

Genetic therapies in accordance with the present invention may involve a transient (temporary) presence of the gene therapy polynucleotide in the patient or the permanent introduction of a polynucleotide into the patient.

Genetic therapies, like the direct administration of agents discussed above, in accordance with the present invention may be used alone or in conjunction with other therapeutic modalities.

Compositions and Administration

Compositions of the present invention comprise an acceptable carrier. Typically, the carrier will also be considered as a "pharmaceutically acceptable carrier", meaning that it is suitable to be administered to an animal, preferably a human. Suitable carriers include isotonic saline solutions, for example phosphate-buffered saline. The compounds of the present invention may be admixed with any suitable binder(s), lubricant(s), suspending agent(s), coating agent(s), solubilising agent(s).

The composition of the invention may be administered by direct injection. The composition may be formulated for, as examples, parenteral, intramuscular, intravenous, subcutaneous, intraocular, oral or transdermal administration. Typically, each protein (for example) may be administered at a dose of from 0.01 to 30 mg/kg body weight, preferably from 0.1 to 10 mg/kg, more preferably from 0.1 to 1 mg/kg body weight. The routes of administration and dosages described are intended only as a guide since a skilled practitioner will be able to determine readily the optimum route of administration and dosage for any particular, compound, animal and condition.

Polynucleotides/vectors encoding polypeptide components may be administered directly as a naked nucleic acid construct, preferably further comprising flanking sequences homologous to the host cell genome. When the polynucleotides/vectors are administered as a naked nucleic acid, the amount of nucleic acid administered may typically be in the range of from 1 μg to 10 mg, preferably from 100 μg to 1 mg. Uptake of naked nucleic acid constructs by mammalian cells is enhanced by several known transfection techniques for example those including the use of transfection agents. Examples of these agents include cationic agents (for example calcium phosphate and DEAE-dextran) and lipofectants (for example lipofectam™ and transfectam™). Typically, nucleic acid constructs are mixed with the transfection agent to produce a composition.

A SOCS protein which lacks, or has an inactivated, PEST domain, can be formulated and administered to a subject in a similar manner to that as described by Jo et al. (2005), as well as outlined in WO 05/086800. Jo et al. produced a cell-penetrating fusion protein of SOCS3 which, when administered, suppressed inflammatory responses.

One embodiment of the present invention is a controlled release formulation that is capable of slowly releasing a composition of the present invention into an animal. As used herein, a controlled release formulation comprises a composition of the present invention in a controlled release vehicle. Suitable controlled release vehicles include, but are not limited to, biocompatible polymers, other polymeric matrices, capsules, microcapsules, microparticles, bolus preparations, osmotic pumps, difflusion devices, liposomes, lipospheres, and transdermal delivery systems. Preferred controlled release formulations are biodegradable (i.e., bioerodible).

The compositions can be formulated into tablets or capsules and administered singly or two or more at a time, as appropriate.

Typically, the physician will determine the actual dosage which will be most suitable for an individual patient and it will vary with the age, weight and response of the particular patient. The above dosages are exemplary of the average case.

There can, of course, be individual instances where higher or lower dosage ranges are merited, and such are within the scope of this invention.

For some applications, preferably the compositions are administered orally in the form of tablets containing excipients such as starch or lactose, or in capsules or ovules either alone or in admixture with excipients, or in the form of elixirs, solutions or suspensions containing flavouring or colouring agents.

For parenteral administration, the compositions are best used in the form of a sterile aqueous solution which may contain other substances, for example enough salts or monosaccharides to make the solution isotonic with blood.

The routes of administration and dosages described are intended only as a guide since a skilled practitioner will be able to determine readily the optimum route of administration and dosage for any particular patient depending on, for example, the age, weight and condition of the patient.

Proteins

As used herein, the terms "polypeptide" and "protein" are used interchangeably.

The % identity of a polypeptide is determined by GAP (Needleman and Wunsch, 1970) analysis (GCG program) with a gap creation penalty=5, and a gap extension penalty=0.3. The query sequence is at least 15 amino acids in length, and the GAP analysis aligns the two sequences over a region of at least 15 amino acids. More preferably, the query sequence is at least 50 amino acids in length, and the GAP analysis aligns the two sequences over a region of at least 50 amino acids. Even more preferably, the query sequence is at least 100 amino acids in length and the GAP analysis aligns the two sequences over a region of at least 100 amino acids. Even more preferably, the GAP analysis aligns the two sequences over their entire length.

In embodiments of the invention, the SOCS protein which lacks a PEST domain, or has an inactivated PEST domain, is at least 85%, more preferably at least 90%, even more preferably at least 95%, even more preferably at least 97%, and most preferably at least 99% identical to a sequence provided in SEQ ID NO's: 3 or 4.

As used herein a "biologically active" fragment is a portion of a polypeptide defined herein which maintains a defined activity of the full-length polypeptide. In a particularly preferred embodiment, the biologically active fragment is able to inhibit LIF-induced Stat3 activity. Biologically active fragments can be any size as long as they maintain the defined activity.

Typically, a protein of the invention is substantially purified. By "substantially purified" we mean a protein that has generally been separated from the lipids, nucleic acids, other peptides, and other contaminating molecules with which it is associated in its native state. Preferably, the substantially purified protein is at least 60% free, more preferably at least 75% free, and more preferably at least 90% free from other components with which it is naturally associated.

Amino acid sequence mutants of the proteins of the present invention can be prepared by introducing appropriate nucleotide changes into a nucleic acid of the present invention, or by in vitro synthesis of the desired polypeptide. Such mutants include, for example, deletions, insertions or substitutions of residues within the amino acid sequence. A combination of deletion, insertion and substitution can be made to arrive at the final construct, provided that the final protein product possesses the desired functional characteristics.

In designing amino acid sequence mutants, the location of the mutation site and the nature of the mutation will depend on characteristic(s) to be modified. The sites for mutation can be modified individually or in series, e.g., by (1) substituting first with conservative amino acid choices and then with more radical selections depending upon the results achieved, (2) deleting the target residue, or (3) inserting other residues adjacent to the located site.

Amino acid sequence deletions generally range from about 1 to 30 residues, more preferably about 1 to 10 residues and typically about 1 to 5 contiguous residues.

Substitution mutants have at least one amino acid residue in the polypeptide molecule removed and a different residue inserted in its place. The sites of greatest interest for substitutional mutagenesis include sites identified as not being essential for cell signalling, such as binding to gp130, or regions of the PEST domain which regulate protein degradation. Sites falling within a sequence of at least three other identically conserved sites, are preferably substituted in a relatively conservative manner. Such conservative substitutions are shown in Table 2.

The present invention relates, in part, to a SOCS protein which lacks, or has an inactivated, PEST domain. Preferably, the SOCS protein is SOCS3. The SOCS protein which lacks a PEST domain may have a sequence as provided in SEQ ID NO's 3 or 4. In these instances the PEST domain was substituted with the unstructured linker motif GSGSGSGS (SEQ ID NO:10), however, the skilled person could readily identify other sequences which can be used as a substitute for the PEST domain. The size, sequence, and/or presence of the linker motif is unimportant as long as at least one biological function of the SOCS protein is maintained and stability of the modified SOCS protein is enhanced when compared to the native protein. The skilled person could readily make alternate substitutions without removing all biological activities of the protein, for example, whilst maintaining the ability to inhibit LIF-induced Stat3 activity.

In a preferred embodiment, the SOCS protein which lacks a PEST domain, or has an inactivated PEST domain, is SOCS3, and the protein at least comprises amino acids 22 to 128 and 164 to 185 of SEQ ID NO:2.

TABLE 2

Exemplary Substitutions

| Original Residue | Exemplary Substitutions |
|---|---|
| Ala (A) | val; leu; ile; gly |
| Arg (R) | lys |
| Asn (N) | gln; his |
| Asp (D) | glu |
| Cys (C) | ser |
| Gln (Q) | asn; his |
| Glu (E) | asp |
| Gly (G) | pro, ala |
| His (H) | asn; gln |
| Ile (I) | leu; val; ala |
| Leu (L) | ile; val; met; ala; phe |
| Lys (K) | arg |
| Met (M) | leu; phe |
| Phe (F) | leu; val; ala |
| Pro (P) | gly |
| Ser (S) | thr |
| Thr (T) | ser |
| Trp (W) | tyr |
| Tyr (Y) | trp; phe |
| Val (V) | ile; leu; met; phe, ala |

The SOCS protein which lacks, or has an inactivated, PEST domain of the invention can also be fuised with a cell-penetrating motif, with the resulting protein having a longer lasting effect in vivo when compared to a SOCS fusion protein with a native PEST domain. An example of such a cell-penetrating motif is AAVLLPVLLAAP (SEQ ID NO: 17) described in WO 05/086800. Other cell-penetrating motifs are described in U.S. Pat. Nos. 5,807,746, 6,043,339, 6,495,518, 6,248,558, 6,432,680, 6,780,843, WO 99/49879 and WO 01/37821. Another example of a cell-penetrating fusion protein of the invention comprises a SOCS protein which lacks, or has an inactivated, PEST domain fused to portions of the HIV tat protein. Such HIV tat fusion proteins can be prepared using a SOCS protein which lacks, or has an inactivated, PEST domain, fused to portions of the HIV tat protein as generally described in WO 94/04686 and U.S. Pat. No. 6,316,003.

In another preferred embodiment, the SOCS protein which lacks a PEST domain, or has an inactivated PEST domain, is SOCS3, and the protein at least comprises amino acids 22 to 128 and 164 to 185 of SEQ ID NO:2, and SEQ ID NO: 17.

A SOCS protein with an inactivated PEST domain can readily be identified using techniques known in the art. For example, targeted amino acid substitutions can be made in the PEST domain, and the resulting mutants screened for stability and biological activity using assays described herein. Mutants with enhanced stability, and that maintain at least some (preferably at least 50% when compared to the native protein) ability to inhibit LIF-induced Stat3 activity can be considered as having an inactivated PEST domain.

Furthermore, if desired, unnatural amino acids or chemical amino acid analogues can be introduced as a substitution or addition into the polypeptides of the present invention. Such amino acids include, but are not limited to, the D-isomers of the common amino acids, 2,4-diaminobutyric acid, α-amino isobutyric acid, 4-aminobutyric acid, 2-aminobutyric acid, 6-amino hexanoic acid, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, β-alanine, fluoro-amino acids, designer amino acids such as β-methyl amino acids, Cα-methyl amino acids, Nα-methyl amino acids, and amino acid analogues in general.

Also included within the scope of the invention are polypeptides of the present invention which are differentially modified during or after synthesis, e.g., by biotinylation, benzylation, glycosylation, acetylation, phosphorylation, amidation, derivatization by known protecting/blocking groups, proteolytic cleavage, linkage to an antibody molecule or other cellular ligand, peptide epitope tag etc. These modifications may serve to increase the stability and/or bioactivity of the polypeptide of the invention.

Polypeptides of the present invention can be produced in a variety of ways, including production and recovery of natural proteins, production and recovery of recombinant proteins, and chemical synthesis of the proteins. In one embodiment, an isolated polypeptide of the present invention is produced by culturing a cell capable of expressing the polypeptide under conditions effective to produce the polypeptide, and recovering the polypeptide. A preferred cell to culture is a recombinant cell of the present invention. Effective culture conditions include, but are not limited to, effective media, bioreactor, temperature, pH and oxygen conditions that permit protein production. An effective medium refers to any medium in which a cell is cultured to produce a polypeptide of the present invention. Such medium typically comprises an aqueous medium having assimilable carbon, nitrogen and phosphate sources, and appropriate salts, minerals, metals and other nutrients, such as vitamins. Cells of the present invention can be cultured in conventional fermentation bioreactors, shake flasks, test tubes, microtiter dishes, and petri plates. Culturing can be carried out at a temperature, pH and oxygen content appropriate for a recombinant cell. Such culturing conditions are within the expertise of one of ordinary skill in the art.

Polynucleotides and Genetic Constructs

Typically, a polynucleotide of the invention is "isolated". By an "isolated polynucleotide", including DNA, RNA, or a combination of these, single or double stranded, we mean a polynucleotide which is at least partially separated from the polynucleotide sequences with which it is associated or linked in its native state. Preferably, the isolated polynucleotide is at least 60% free, preferably at least 75% free, and most preferably at least 90% free from other components with which they are naturally associated. Furthermore, the term "polynucleotide" is used interchangeably herein with the term "nucleic acid".

The % identity of a polynucleotide can be determined by GAP (Needleman and Wunsch, 1970) analysis (GCG program) with a gap creation penalty=5, and a gap extension penalty=0.3. Unless stated otherwise, the query sequence is at least 45 nucleotides in length, and the GAP analysis aligns the two sequences over a region of at least 45 nucleotides. Preferably, the query sequence is at least 150 nucleotides in length, and the GAP analysis aligns the two sequences over a region of at least 150 nucleotides. Even more preferably, the GAP analysis aligns the two sequences over their entire length.

With regard to the defined polynucleotides, it will be appreciated that % identity figures higher than those provided above will encompass preferred embodiments. Thus, where applicable, in light of the minimum % identity figures, it is preferred that the polynucleotide comprises a polynucleotide sequence which is at least 85%, more preferably at least 90%, more preferably at least 95%, more preferably at least 97%, and even more preferably at least 99% identical to the relevant nominated SEQ ID NO.

One embodiment of the present invention includes a recombinant vector, which includes at least one isolated polynucleotide molecule of the present invention, inserted into any vector capable of delivering the polynucleotide molecule into a host cell. Preferably, the polynucleotide encodes a SOCS protein which lacks, or has an inactivated, PEST domain. Such a vector contains heterologous polynucleotide sequences, that is polynucleotide sequences that are not naturally found adjacent to polynucleotide molecules of the present invention and that preferably are derived from a species other than the species from which the polynucleotide molecule(s) are derived. The vector can be either RNA or DNA, either prokaryotic or eukaryotic, and typically is a virus or a plasmid.

One type of recombinant vector comprises a polynucleotide molecule of the present invention operatively linked to an expression vector. The phrase operatively linked refers to insertion of a polynucleotide molecule into an expression vector in a manner such that the molecule is able to be expressed when transformed into a host cell. As used herein, an expression vector is a DNA or RNA vector that is capable of transforming a host cell and of effecting expression of a specified polynucleotide molecule. Preferably, the expression vector is also capable of replicating within the host cell. Expression vectors can be either prokaryotic or eukaryotic, and are typically viruses or plasmids. Expression vectors of the present invention include any vectors that function (i.e., direct gene expression) in recombinant cells of the present invention, including in bacterial, flngal, endoparasite, arthropod, other animal, and plant cells. Preferred expression vectors of the present invention can direct gene expression in bacterial, yeast, plant and mammalian cells, and more preferably in the cell types disclosed herein.

In particular, expression vectors of the present invention contain regulatory sequences such as transcription control sequences, translation control sequences, origins of replication, and other regulatory sequences that are compatible with the recombinant cell and that control the expression of polynucleotide molecules of the present invention. In particular, recombinant molecules of the present invention include transcription control sequences. Transcription control sequences are sequences which control the initiation, elongation, and termination of transcription. Particularly important transcription control sequences are those which control transcription initiation, such as promoter, enhancer, operator and repressor sequences. Suitable transcription control sequences include any transcription control sequence that can function in at least one of the recombinant cells of the present invention.

Host Cells

Another embodiment of the present invention includes a recombinant cell comprising a host cell transformed with one or more recombinant molecules of the present invention. Transformation of a polynucleotide molecule into a cell can be accomplished by any method by which a polynucleotide molecule can be inserted into the cell. Transformation techniques include, but are not limited to, transfection, electroporation, microinjection, lipofection, adsorption, and protoplast fusion. A recombinant cell may remain unicellular or may grow into a tissue, organ or a multicellular organism. Transformed polynucleotide molecules of the present invention can remain extrachromosomal or can integrate into one or more sites within a chromosome of the transformed (i.e., recombinant) cell in such a manner that their ability to be expressed is retained.

Suitable host cells to transform include any cell that can be transformed with a polynucleotide of the present invention. Host cells of the present invention either can be endogenously (i.e., naturally) capable of producing proteins of the present invention or can be capable of producing such proteins after being transformed with at least one polynucleotide molecule of the present invention. Host cells of the present invention can be any cell capable of producing at least one protein of the present invention, and include bacterial, fungal (including yeast), parasite, arthropod, animal and plant cells. Preferred host cells include bacterial, mycobacterial, yeast, arthropod and mammalian cells. More preferred host cells include *Salmonella, Escherichia, Bacillus, Listeria, Saccharomyces, Spodoptera, Mycobacteria, Trichoplusia,* BHK (baby hamster kidney) cells, MDCK cells (normal dog kidney cell line for canine herpesvirus cultivation), CRFK cells (normal cat kidney cell line for feline herpesvirus cultivation), CV-1 cells (African monkey kidney cell line used, for example, to culture raccoon poxvirus), COS (e.g., COS-7) cells, and Vero cells. Particularly preferred host cells are *E. coli*, including *E. coli* K-12 derivatives; *Salmonella typhi; Salmonella typhimurium*, including attenuated strains; *Spodoptera frugiperda; Trichoplusia ni;* BHK cells; MDCK cells; CRFK cells; CV-1 cells; COS cells; Vero cells; and non-tumorigenic mouse myoblast G8 cells (e.g., ATCC CRL 1246). Additional appropriate mammalian cell hosts include other kidney cell lines, other fibroblast cell lines (e.g., human, murine or chicken embryo fibroblast cell lines), myeloma cell lines, Chinese hamster ovary cells, mouse NIH/3T3 cells, LMTK cells and/or HeLa cells. A particularly preferred host cell is a type of cell, preferably a type of human cell, that produces a SOCS3 protein.

Recombinant DNA technologies can be used to improve expression of a transformed polynucleotide molecule by manipulating, for example, the number of copies of the polynucleotide molecule within a host cell, the efficiency with which those polynucleotide molecules are transcribed, the efficiency with which the resultant transcripts are translated, and the efficiency of post-translational modifications. Recombinant techniques useful for increasing the expression of polynucleotide molecules of the present invention include, but are not limited to, operatively linking polynucleotide molecules to high-copy number plasmids, integration of the polynucleotide molecule into one or more host cell chromosomes, addition of vector stability sequences to plasmids, substitutions or modifications of transcription control signals (e.g., promoters, operators, enhancers), substitutions or modifications of translational control signals (e.g., ribosome binding sites, Shine-Dalgarno sequences), modification of polynucleotide molecules of the present invention to correspond to the codon usage of the host cell, and the deletion of sequences that destabilize transcripts.

EXAMPLES

Example 1

Materials and Methods

Cloning and Expression

Fragments of murine SOCS3 corresponding to residues 22-185, 22-225, 22-185(Δ129-163) and 22-225(Δ129-163) were cloned by PCR into a ligation-independent cloning (LIC) vector and expressed. Briefly, for $^{15}$N and $^{13}$C labelling, cells were grown to an $OD_{600}$ of 0.6 in Neidhardt's medium (Neidhardt et al., 1974) containing 1.0 g/L $^{15}NH_4Cl$ and/or 2 g/L $^{13}$C glucose as the sole nitrogen and carbon sources, respectively. Cells were harvested 8 h after IPTG induction by centrifugation at 6200 g at 4° C. for 30 min. All SOCS3 clones express as insoluble inclusion bodies and require refolding.

Protein Purification

Pelleted bacterial cells were resuspended in PBS and then lysed by homogenisation. The lysate was centrifuged at 20,000 g and the pelleted inclusion bodies solubilised using 6M GdnHCl. The protein was then purified using Ni-NTA resin (Qiagen) by binding at pH 8.0, washing at pH 6.3 and eluting at pH 4.5, all in 6M GdnHCl. The eluted protein was diluted to 0.1 mg/mL and a final GdnHCl concentration of 4 M and then refolded by extensive dialysis against 25 mM sodium phosphate, 50 mM sodium chloride, 5 mM 2-mercaptoethanol at pH 6.7. Refolding to the native structure was confirmed by binding an aliquot to a column with immobilised phosphorylated gp130 peptide (STASTVEpYSTV-VHSG, pY=phosphotyrosine; synthesized by Auspep, Melbourne) (SEQ ID NO:11). The same gp130 peptide was added at a 1.5-molar excess to the purified SOCS3 and 50 mM glutamate plus 50 mM arginine added before concentration to 8 mg/mL.

NMR Spectroscopy

Spectra were recorded at 298 K on Bruker Avance 500 (with cryoprobe), DRX-600 and a Varian Unity INOVA 800 spectrometers. Spectra were processed using XWINNMR (Bruker AG, Karlsruhe, Germany) or NMR-pipe and analysed using XEASY (version 1.3.13) or nmrDraw (Delaglio et al., 1995). Spectra were referenced to the $H_2O$ signal at 4.77 ppm (298 K) or a small impurity at 0.15 ppm. $C^\alpha$, $C^\beta$, $H^\alpha$, C' and N chemical shifts were used in the program TALOS (Cornilescu et al., 1999) to obtain backbone torsion angles. Sequence-specific resonance assignments for the backbone were accomplished using HNCA, HN(CO)CA, CBCA(CO) NH, HN(CA)CO and HNCO experiments, and sidechain assignments using $^{15}$N-edited TOCSY-HSQC and NOESY-HSQC, HCCH-TOCSY and HCCH-COSY.

For structure calculations, distance restraints were obtained from $^1$H-$^{15}$N and $^1$H-$^{13}$C edited NOESY-HSQC and two-dimensional $^1$H-$^1$H NOESY experiments. SOCS3, even in the presence of the gp130 phosphopeptide, has low solubility. Because of substantial protein aggregation at the SOCS concentration of 0.4 mM used in our studies, three-dimensional NOESY-HSQC spectra that yield NOE-based distance restraints gave low signal-to-noise ratios, as a result of which the number of NOE restraints obtained was low for a protein of this size. In particular, only methyl-methyl long-range NOEs were detected using $^{13}$C-edited NOESY experiments because of the shorter transverse relaxation times of carbon compared with nitrogen. Exhaustive analysis of 2D $^1$H-$^1$H NOESY experiments performed on the Varian Unity INOVA 800 MHz spectrometer yielded additional NOEs.

In general, non-polar sidechains were well defined whilst polar sidechains were not. Interpretation of inter-atomic distances has therefore been limited solely to those residues where multiple NOEs confirmed their proximity, unless specifically stated otherwise.

Structure Calculation

The solution structure of murine SOCS3 was calculated using a combined torsion angle and Cartesian coordinates dynamics protocol executed in X-PLOR. Structures were calculated from random starting coordinates using 973 NOE distance restraints, including 142 medium-range (residue i to residue i+j, where 1<j<4) and 280 long-range (residue i to residue i+j, where j>4) connectivities, and 160 dihedral angle restraints, composed of 80 phi and 80 psi angles. The structures were displayed and analyzed using Pymol (DeLano, 2004), MolMol (Koradi et al., 1996) and PROCHECK-NMR (Laskowski et al., 1996). The final family comprised the 20 structures of lowest total energy. The coordinates are provided in Table 1.

SOCS3 Expression Constructs and Luciferase Assay

Constructs encoding SOCS3 proteins with an N-terminal Flag epitope tag (DYKDDDDK) (SEQ ID NO: 14) were generated by PCR to give fragments with in-frame Asc I and Mlu I restriction enzyme sites at the N- and C- termini, respectively, and sub-cloned into the mammalian expression vector pEF-FLAG-I, a derivative of the mammalian expression vector pEF-BOS (Mizushima and Nagata, 1990). SOCS3 mutants lacking the PEST sequence were generated using the PCR-based technique, splicing by overlap extension (Horton et al., 1989).

293T cells were transiently transfected with constructs expressing Flag epitope-tagged SOCS3 proteins and a leukaemia inhibitory factor (LIF)-responsive promoter-Firefly luciferase reporter gene (APRE-luc), essentially as described (Nicholson et al., 1999). Cells were incubated overnight with or without 10 ng/ml recombinant human LIF (Amrad, Melbourne, Australia) prior to lysis with 100 µl of Reporter Lysis Buffer (Promega, Madison, Wis.) containing protease inhibitors (Complete Cocktail tablets, Boehringer Mannheim). To control for transfection efficiency, cells were transfected with a vector expressing Renilla luciferase downstream of a Herpes-simplex virus thymidine kinase (HSV-TK) (Promega, Madison Wis.).

Firefly and Renilla luciferase activities were quantified using substrate reagents from the Luciferase Assay Dual-Reporter kit (Promega, Madison Wis.) and an automated LUMIstar Galaxy plate reader (BMG Technologies, Offenburg, Germany). SOCS3 protein expression was analysed by Western blot with polyclonal rat anti-Flag antibody (Drs. D. Huang & L. O'Reilly, The Walter and Eliza Hall Institute of Medical Research, Melbourne, Australia) as described (Nicholson et al., 1999).

In vivo Half-Life Experiments 293T cells ($5\times10^5$ cells/well) were transfected with 1.5 µg of the appropriate SOCS3 expression construct as described above. 48 h after transfection cells were washed twice in PBS and incubated for 1 h in Met/Cys-free DME (Gibco-BRL). Cells were then incubated for 30 min in DME containing 0.15 mCi/ml [$^{35}$S]Met/Cys (Perkin-Elmer) followed by DME+ 10% Foetal calf serum (Sigma)+2 mM Cys+2 mM Met for various times, upon which cells were lysed in KALB lysis buffer (1 mM EDTA, 150 mM NaCl, 50 mM Tris-Cl, 1% Triton X-100, pH 7.5) and the amount of [$^{35}$S]-labelled SOCS3 was determined by immunoprecipitation using anti-Flag tag M2 beads (Sigma). Detection and quantification was carried out using a FujiFilm FLA-3000 phosphoimager and associated software.

Example 2

Expression of SOCS3 Fragments

Two initial constructs of mouse SOCS3 [SOCS3(22-225) and SOCS3(22-185)] were cloned and expressed in E. coli. Both contained the KIR and the extended SH2 domain, but SOCS3(22-185) lacked the C-terminal SOCS box. Both constructs expressed in inclusion bodies in E. coli and required refolding. A phosphotyrosine peptide from gp130 (STASTVEpYSTVVHSG) (SEQ ID NO:11) has been shown previously to bind with high affinity to mouse SOCS3 (Nicholson et al., 2000; Schmitz et al., 2000).

The addition of a molar excess of peptide significantly increased the solubility in NaCl/Pi from <<1 mg·mL$^{-1}$ to ≈1 mg·mL$^{-1}$ for SOCS3(22-225) and to 3 mg·mL$^{-1}$ for SOCS3 (22-185). As SOCS3(22-185) in the presence of the tyrosine-phosphorylated peptide could not be concentrated beyond ≈0.2 mm, seven constructs of shorter length were expressed in E. coli and their solubility examined. All constructs contained the SH2 domain, as defined by sequence homology (Okazaki et al., 2002), but included differing lengths of sequence outside this region.

All seven constructs (22-142, 22-128, 22-126, 44-185, 44-142, 44-128 and 44-126), and the control 22-185 and 22-225 fragments, were expressed in inclusion bodies in E. coli and required refolding. The construct showing the highest solubility was SOCS3(22-185). Constructs shorter than this at the C-terminal end did not bind tightly to the gp130 peptide (data not shown). All of the other constructs had equal or lower solubility, even in the presence of the tyrosine-phosphorylated peptide, including the predicted SH2 domain alone (44-142). This implied that the SH2 domain itself was a cause of poor solubility, as was the SOCS box.

The sequences of the SOCS3 SH2 domain and the phosphatidylinositol (PtdIns) 3-kinase (N-terminal) SH2 domain (the SH2 domain with the highest sequence identity in the PDB) were therefore aligned and hydrophobic residue substitutions in SOCS3 that were surface-exposed in the PtdIns 3-kinase structure were considered as candidates for point mutagenesis. Six residues that were solvent-exposed and hydrophilic in PtdIns 3-kinase but not in SOCS3 were identified and mutated to match the PtdIns 3-kinase residue. The six mutants (A50D, G53R, L58E, A62E, A65E, G99D) were all cloned and expressed in E. coli as part of a 22-185 construct. All six constructs again expressed in inclusion bodies and required refolding. The maximum concentration obtained by any of the six point mutants was ≈3 mg·mL$^{-1}$, in the presence of peptide, no higher than the wild-type SOCS3 (22-185) construct. As SOCS3(22-225) was too poorly soluble to obtain any meaningful structural data, the wild-type SOCS3(22-185) construct was pursued.

Example 3

NMR Assignments for Murine SOCS3$_{(22-185)}$

After buffer optimization, SOCS3(22-185) was soluble to ≈0.5 mM, but UV-visible spectra of the protein showed that significant aggregation was occurring at this concentration, indicated by a high apparent absorption at 320 nm as a result of scattering. Many NMR experiments required for full protein assignment therefore did not yield acceptable results, in particular HNCACB, HCCH-TOCSY and $^{13}$C-NOESY-HSQC. Nevertheless, near-complete backbone resonance assignments were made for SOCS3(22-185).

Apart from five missing spin systems (Ser25-Ser28 and Gly170), 100% of $^1$HN, 100% of $^{15}$N (excluding 18 proline residues), 96% of $^{13}$C$_\alpha$, 84% of 13C$_\beta$, 87% of $^{13}$C' and 84% of $^1$Hα were assigned unambiguously (FIG. 2). HNCO experiments were used to obtain $^{13}$C' resonances and therefore all $^{13}$C' N-terminal to proline residues remain unassigned. The majority of side-chain assignments were determined, but because of the poor spectral quality of HCCH-TOCSY and $^{13}$C NOESY-HSQC experiments, no hydrophilic or polar γ, δ or ε carbon assignments were made. Secondary structure elements were determined by analysis of backbone and $^{13}$C$_\beta$ chemical shifts, from characteristic NOE patterns in the $^{15}$N-edited NOESY-HSQC and by using TALOS (Cornilescu et al., 1999). Assignments revealed that SOCS3 had an ααββββαβββ topology, with the ESS and the C-terminal end of KIR forming the first α-helix (FIG. 2). Significantly, there was a large unstructured region between Met128 and Arg163 that contained a high proportion of proline residues (12 out of 35).

Example 4

SOCS3 Contains a PEST Region

The sequence of the unstructured region of murine SOCS3 is highly conserved in mammalian SOCS3, as shown in FIG. 3. This region displays all of the common features of PEST sequences (Rogers et al., 1986), namely a high proportion of Pro, Glu, Ser and Thr residues, the absence of Lys, His and Arg except at the termini, and the fact that it is completely unstructured based on the absence of medium- and long-range NOEs and the observation of intense backbone amide peaks.

The primary sequence of SOCS3 was analysed for the presence of a PEST sequence by using the PESTfind program www.at.embnet.org/embnet/tools/bio/PESTfind (Rechsteiner and Rogers, 1996). This analysis identified the likely presence (PESTfind score +11.11 (Rechsteiner and Rogers, 1996)) of a single PEST sequence in SOCS3 spanning residues His126-Lys162. The unstructured region of SOCS3 spans Met128-Arg163 and therefore matches almost exactly the predicted PEST region. Residues from Met128-Arg163 showed no inter-residue NOEs other than sequential connectivities, did not have restrained φψ angles according to TALOS, had amide resonances in the random coil region of the $^{15}$N-HSQC spectrum and showed significantly narrower line-widths than any other residues in the protein. This indicates that the PEST sequence is an unstructured, highly mobile region within SOCS3.

Example 5

The PEST Sequence is an Insertion in the SH2 Domain

Analysis of the secondary structure of SOCS3, and sequence alignments with SH2 domains, reveals that the PEST sequence begins immediately after the last residue of helix B in the SH2 domain. However, most SH2 domains do not end with this helix, but contain further structural elements at their C termini, including the 'BG loop' and the 'G'-strand (FIG. 2) (Grucza et al., 1999). Hortner et al. (2002b) have modelled the structure of the SOCS3 SH2 domain and suggest that the BG loop and βG strand are formed from residues Gly132-Val148, which we have shown to be unstructured and part of the PEST region.

The inventors examined the sequence of the 19 structured residues immediately downstream of the PEST region and found a high likelihood that they constitute the BG loop and βG strand of the SH2 domain of SOCS3. In particular, Leu176-Leu182 aligned well with the seven C-terminal residues of a number of SH2 domains, supporting this hypothesis. In agreement with this scenario, deletion of residues 182-185 had been shown previously to affect phosphotyrosine peptide binding (Sasaki et al., 1999). Although the sequence between Tyr165 and Pro175, which would form the 'BG loop', was not significantly similar to other SH2 domains, the SHP-2 (Waksman et al., 1993), grb7 (Brescia et al., 2002) and, in particular, STAT3b (Becker et al., 1998) SH2 domains contain extended loops in this region that structurally resemble a β-hairpin. Analysis of the secondary structure of SOCS3 shows that it forms a β-hairpin in this region. Thus, it appears that the PEST sequence constitutes an insertion in the true SOCS3 SH2 domain.

Example 6

Murine SOCS3(Δ129-163) Binds to a Phosphotyrosine Peptide from gp130

In order to determine whether deleting the PEST region would have an impact on the function of the SH2 domain, binding studies and isothermal titration calorimetry (ITC) were performed using a 22-185 construct lacking the PEST region [SOCS3(22-185)(Δ129-163)] and the tyrosine phosphorylated peptide from gp130. SOCS3(Δ129-163) was constructed by replacing Pro129-Arg163 inclusive, with an eight residue [(Gly-Ser)×4] linker in the 22-185 construct. As shown in FIG. 4, the construct lacking the PEST region binds to the gp130 peptide. ITC analyses showed that the titration curve could be fitted using a single binding site mode with a K$_d$ of 74±7 nm. The K$_d$ of wild-type SOCS3(22-185) binding was 152±25 nm.

Example 7

PEST Sequences in Other SOCS Family Proteins

In order to determine whether other members of the SOCS family contained PEST motifs, their sequences were analysed using the PESTfind algorithm (Rechsteiner and Rogers, 1996). Of the eight members of the murine SOCS family, SOCS1, -3, -5 and -7, and CIS, show a PEST motif with a PESTfind score of >5. CIS and SOCS3 have the PEST motif within the SH2 domain, while SOCS1, -5 and -7 contain PEST motifs in the N-terminal domain (FIG. 5). The PEST sequence in the CIS SH2 domain is located eight residues downstream from the terminus of the predicted αB helix.

Example 8

Tertiary Structure of Murine SOCS3$_{22-185}$

As the solubility of full-length SOCS3 is too low for structure determination we determined the solution structure of SOCS3 lacking the C-terminal SOCS box, using a construct that spanned residues 22-185. This includes the Kinase Inhibitory Region (KIR), N-terminal extended SH2 subdomain, SH2 domain and the C-terminal extended SH2 subdomain. Structural statistics are summmarized in Table 3. As the tyrosine-phosphorylated gp130 peptide was bound to SOCS3 in all NMR experiments we also determined the structure of eight consecutive residues in the peptide that interact directly with SOCS3. Other residues in the peptide could not be assigned but are not expected to interact with SOCS3 based on previous mutagenesis studies (Nicholson et al., 2000).

The tertiary fold of murine SOCS3$_{22-185}$ (FIG. 6) is that of a classical SH2 domain but with a 15-residue α-helix (Glu30-Ser44) immediately upstream which directly contacts the phosphotyrosine binding loop and in part determines its geometry. The first half of the Kinase Inhibitory Region (KIR) is unstructured. The SH2 domain is formed by residues Gly45-Asn185, excluding an unstructured insertion of 35 residues (Pro129-Arg163).

TABLE 3

Summary of experimental restraints and structural statistics for mouse SOCS3.

| | |
|---|---|
| no. of distance restraints | 973 |
| intraresidue (i = j) | 274 |
| sequential (\|i − j\| = 1) | 277 |
| medium-range (1 < \|i − j\| < 4) | 142 |
| long-range (\|i − j\| > 4) | 280 |
| Total dihedral angle restraints | 160 |
| φ angles | 80 |
| Ψ angles | 80 |
| Violations | |
| NOE violations >0.3 Å | 0 |
| Dihedral violations >5° | 1 |
| energies | |
| E$_{NOE}$ (kcal mol$^{-1}$)$^a$ | 7.47 ± 1.23 |
| E$_{dihe}$ (kcal mol$^{-1}$) | 6.30 ± 1.72 |
| deviations from ideal geometry$^b$ | |
| bonds (Å) | 0.0017 ± 0.0006 |
| angles (deg) | 0.551 ± 0.003 |
| impropers (deg) | 0.410 ± 0.008 |
| Average rmsd to mean atomic coordinates (Å) | |
| Secondary Structure elements (N, C$^α$, C') | 0.95 Å |
| Secondary Structure elements (all heavy atoms) | 1.47 Å |
| Ordered regions, 30-104, 119-128, 164-184, (N, C$^α$, C') | 1.24 Å |
| Ordered regions, 30-104, 119-128, 164-184, (all heavy atoms) | 1.79 Å |

| Ramachandran plot$^d$ | Residues 30-185 | Ordered regions (30-104, 119-128, 164-184) |
|---|---|---|
| most favored (%) | 68.3 | 82.0 |
| additionally allowed (%) | 21.5 | 11.9 |

TABLE 3-continued

Summary of experimental restraints and structural statistics for mouse SOCS3.

| | | |
|---|---|---|
| generously allowed (%) | 7.6 | 4.9 |
| disallowed (%) | 2.7 | 1.1 |

$^a$The values for ENOE are calculated from a square well potential with force constants of 50 kcal mol$^{-1}$ Å$^2$.
$^b$The values for the bonds, angles, and impropers show the deviations from ideal values based on perfect stereochemistry.
$^c$RMSD over the backbone heavy atoms (N, C$^α$, C').
$^d$As determined by the program PROCHECK-NMR for all residues except Gly and Pro (Laskowski et al., 1996). The PEST motif was completely unrestrained in all structure calculations which leads to poor Ramachandran statistics for that region, therefore the analysis is shown with the PEST motif removed as well.

Example 9

Structure of the SH2 Domain

The SH2 domain of murine SOCS3 consists of a central, three-stranded, β-sheet flanked by an α-helix on each face. Helix A (residues 52-62), unusually for SH2 domains, begins with a Gly-Gly pair situated directly above the conserved arginine (Arg71) that interacts with the phosphate group of p-Tyr in all SH2 domains studied to date. The N-terminus of this helix is consistent with an N-terminal capping box (Harper and Rose, 1993) formed by residues Thr52 and Glu55 and a hydrophobic staple (Munoz et al., 1995) formed by residues Val51 and Ala56. These appear to determine the geometry of helix A in relation to the preceding residues.

The central β-sheet (residues 67-94) is followed by a short β-hairpin turn (residues 96-103) and loop (residues 105-119), then helix B (residues 120-128), which is amphipathic and makes a number of hydrophobic contacts with the domain core, in particular via the side chains of Val120, Leu123 and Tyr127.

Following Met129, the C-terminal residue of helix B, there is a 35-residue insertion, the PEST motif. This displays no evidence of structure and backbone amide NMR relaxation data suggests a high degree of flexibility. The N- and C-termini of the PEST motif are very close together, with the C$^α$ atoms lying within 8 Å of each other. This indicates that the PEST motif is a true insertion into the SH2 domain, being located between two secondary structural elements, the αB helix and the BG loop. The BG loop and βG strand (residues 164-185), located downstream of the PEST insertion, contact the rest of the domain in a similar manner to that seen in other SH2 domains.

The lowest energy structure of the final ensemble was used in the program DALI (Holm and Sander, 1995) to determine the closest structural neighbour to the SH2 domain of SOCS3 in the PDB. The highest structural similarity was to that of the C-terminal SH2 domain of SHP-2, with an r.m.s.d of 2.9 Å over 91 residues.

Example 10

The 20 Residues Immediately Downstream of the PEST Motif Form the BG Loop and βG Strand of the SH2 Domain The BG loop has an important role in determining substrate specificity in a number of SH2 domains, contacting residues downstream from the pTyr itself (Grucza et al., 1999). As in the SH2 domain of Stat3b (Becker et al., 1998), the BG loop in SOCS3 is actually a β-hairpin rather than a loop. In SOCS3, it is formed from residues immediately downstream of the PEST insertion (FIG. 6, Panel B) and is mostly hydrophobic, the sequence being AYYIYSGGEKIPL. In particular, the inner surface, which contacts the pTyr-peptide, is completely hydrophobic.

The BG loop itself makes very few contacts with the rest of the domain, with only the first and last residues (Tyr165 and Leu176) showing significant interactions with the domain core. Instead, the loop is held in position by the pTyr peptide. It is attached to the rest of the SH2 domain primarily by a string of hydrophobic interactions involving residues downstream. In particular, Leu176, Val177, Leu178 and Leu182 make van der Waals contacts with hydrophobic residues from the central β-sheet. Previous mutagenesis results have shown that deletion of Leu182 and upstream residues abolishes the ability of SOCS3 to bind pTyr-peptides (Sasaki et al., 1999).

Example 11

Interactions Between the pTyr-gp130 Peptide and the SH2 Domain

The gp130 peptide, when bound to SOCS3, is centred in the middle of one edge of the central sheet and lies orthogonal to the direction of the strands themselves. It interacts with two hydrophobic patches on the surface of the SH2 domain. Residues upstream of the pTyr interact with a hydrophobic area formed primarily by two adjacent glycines near the N-terminus of helix A, whilst residues downstream of the pTyr interact with the BG loop (FIG. 7, Panel A).

Previous alanine scanning of the pTyr-gp130 peptide (Nicholson et al., 2000) has shown that, unlike most SH2 domains, substrate specificity for SOCS3 is determined partly by residues upstream of the phosphotyrosine. In particular, there is a requirement for Val at position −2, with affinity being reduced five-fold when this Val is mutated to Ala and nearly ten-fold when it is deleted altogether. As noted previously (Hortner et al., 2002), the SOCS3 SH2 domain is unusual in containing a Gly-Gly motif near the start of helix A rather than the Arg/Lys-X motif more common in other SH2 domains. Val-2 in the peptide makes hydrophobic contacts with both of these glycines, and a larger, charged residue at these positions would not allow this interaction (Hortner et al., 2002).

Downstream of the pTyr in the gp130 phosphopeptide, the most significant residues are those of Val+3 and Val+4; mutation of these to Ala decreases affinity 31-fold and ten-fold, respectively. This is explained by the structure as both of these valines show significant hydrophobic contacts with the internal surface of the hydrophobic BG loop.

The sidechain geometries of the pTyr and the conserved arginine, Arg71, could not be determined precisely from our structural data. It is clear however, that the pTyr is located close to a positively-charged patch on the surface of the domain formed by Arg71 and 94. Mutagenesis experiments (Sasaki et al., 1999) have shown that mutation of Arg71 will abolish pTyr binding, and all SH2 domains studies so far have shown direct contacts between this conserved arginine and the negative phosphate group on the pTyr itself. Thus, it is highly likely that the guanidine moiety of Arg71 is directly involved in phosphate binding, as it is in all SH2 domains.

Example 12

Structure of the N-terminal Extended SH2 Subdomain and its Effect on pTyr Peptide Binding The extended SH2 subdomain was first identified through the observation that mutations in the 12 residues immediately upstream of the SH2 domain (Val34-Gly45) could disrupt SOCS3 interaction with the tyrosine-phosphorylated activation loop of JAK2 (Sasaki et al., 1999). Our structure of SOCS3 shows that this region forms a completely amphipathic helix, with the hydrophobic side stacking onto the SH2 domain on the opposite face of the central β-sheet to the pTyr binding site (FIG. 7, Panel B). This helical SH2 domain extension interacts directly with residues flanking the pTyr binding loop (BC loop) of the SH2 domain and thus, in part, determines the position of that loop. In particular, Leu41, Val38 and Val34 all interact with Phe80, while Leu41 also interacts with Ile70. Other contacts between the SH2 domain extension and pTyr binding loop are mediated by Tyr47 and Trp48. Mutation of either Val34 or Leu41 has been shown to abolish pTyr binding (Sasaki et al., 1999), suggesting that contacts between these two residues and the BC loop are structurally necessary for pTyr binding.

Mutations in the KIR interfere with JAK2 inhibitory activity in overexpression studies, and the KIR has been proposed to act as a JAK pseudosubstrate, blocking further kinase activity (Yasukawa et al., 1999). The final four residues of the KIR form the N-terminal end of the helical SH2 domain extension and are mostly solvent exposed. This includes Tyr31, a residue that disrupts JAK kinase inhibition when mutated. The first half of the KIR is unstructured and completely solvent exposed, at least in the absence of JAK.

Example 13

The PEST Motif is not Important Structurally and is not Involved in STAT Inhibition The present inventors have shown that removing the PEST motif (Pro129-Arg163 inclusive) and replacing it with (Gly-Ser)$_{x4}$ does not disrupt the SH2 domain interaction with a pTyr-peptide from the gp130 receptor. Therefore the structure of this ΔPEST-SOCS3 construct was analysed by recording a $^{15}$N-HSQC spectrum and comparing it with wild-type SOCS3. Changes in chemical shift were generally below 0.1 ppm (FIG. 8, Panel A) except for residues near the boundaries of the (Gly-Ser)$_{x4}$ insertion (Val124-Met128 and Ala164-Tyr165). Val177-Ser179 also showed significant chemical shift changes; in the wild-type structure these residues lie directly above and within 5 Å of the first residue of the PEST motif, so it is likely that they are slightly affected by the (Gly-Ser)$_{x4}$ insertion due to their spatial proximity.

As removing the PEST sequence did not alter the SH2 domain structure, we investigated whether this construct maintained activity in vivo. The ability of SOCS3 lacking the PEST sequence to inhibit Stat3 activity was tested using a Stat3-reponsive luciferase assay. 293T cells were transiently transfected with constructs expressing Flag-tagged SOCS3, SOCS3 lacking the PEST sequence (ΔPEST), SOCS3 lacking the SOCS box (ΔSB) or SOCS3 lacking both (ΔPEST/ΔSB). As shown in FIG. 8, Panel B, deletion of the PEST sequence did not alter the ability of SOCS3 to inhibit LIF-induced Stat3 activity. As expected, the SOCS3 inhibitory activity was also maintained in the absence of both the SOCS box and PEST sequence. Western blot of cell lysates with anti-Flag-antibodies demonstrated equivalent levels of SOCS3 proteins.

Example 14

The PEST Motif Regulates Protein Stability

Intracellular levels of SOCS3 are strongly regulated by proteolysis. Two regions of the protein have been implicated previously in regulating proteolysis, Lys6 in the N-terminal domain and the C-terminal SOCS box (Chen et al., 2002; Kamura et al., 1998; Sasaki et al., 2003). As PEST motifs are known to be signals for protein degradation in vivo (Rogers et al., 1986), we measured the half-life of SOCS3 proteins that lacked the PEST motif, as well as constructs lacking the SOCS box and the N-terminal region. Pulse-chase experiments performed in 293T cells show that removing the PEST motif significantly decreased SOCS3 turnover (FIG. 9, Panel A). As the SOCS box and the N-terminal domains also affect SOCS3 turnover we further examined the effect of deleting these regions. The decrease in SOCS3 degradation upon removing the PEST motif from either the full-length protein (upper panel) or from SOCS3$_{22-185}$ (which lacks both the N-terminal domain and SOCS box, lower panel) was significant. Removing the PEST motif had a larger effect on SOCS3 stability than did removing both the SOCS box and N-terminal domain. The construct lacking all three regions showed the lowest level of protein degradation.

As PEST motifs have been associated with proteasome-mediated degradation, we investigated whether proteasome inhibitors would have an effect on the half-life of SOCS3 in 293T cells. As shown in FIG. 9, Panel B, the proteasomal inhibitor MG132 did not affect the half-life of wild-type SOCS3, but it dramatically increased the half-life of ΔPEST SOCS3. After 8 hr in the presence of MG132 approximately 65% of ΔPEST SOCS3 remained, compared with ca. 45% in its absence. After the same time interval only 25% of wild-type SOCS3 remained. Thus it appears that, in 293T cells, the proteasomal pathway is an important route for ΔPEST SOCS3 degradation but that wild-type SOCS3, which contains the PEST motif, is efficiently degraded via another mechanism.

Example 15

Discussion

The structure of SOCS3 explains a number of previous findings regarding functionally important regions of the protein. SOCS3$_{22-185}$ consists of an SH2 domain with a structurally important α-helical N-terminal extension interacting directly with residues near the pTyr binding site, an unstructured PEST insertion between the αB helix and the BG loop, and unstructured residues forming the majority of the KIR. The SH2 domain itself shows closest structural similarity with the C-terminal SH2 domain of SHP-2.

The structure of the SOCS3 phosphopeptide complex shows that, apart from interactions with the phosphotyrosine itself, binding specificity is generated via a number of hydrophobic interactions between the peptide and SOCS3. The peptide shows at least seven residues interacting with SOCS3, which makes this binding motif significantly longer than for most other SH2 domains and explains why the binding affinity of the SOCS3 SH2 domain for the gp130 peptide is high compared to many other SH2 domain/ligand interactions (Ladbury et al., 1995).

The hydrophobic BG loop is a tight β-hairpin turn in SOCS3 and does not interact with the rest of the domain except through single residues at both the N- and C-termini of the loop. Whilst the C-terminus of the BG loop precedes a stretch of hydrophobic residues that fix the position of the loop relative to the rest of the domain, the N-terminus is held in position only by interactions with Tyr165.

The N- and C-terminal SH2 domain extensions represent interesting features of SOCS3. We now see that the C-terminal extension is part of the SH2 domain whilst the N-ESS is an addition to the standard SH2 domain and directly contacts residues important for phosphotyrosine binding. The N-ESS helix contacts the SH2 domain via hydrophobic interactions arising from Val34, Val38 and Leu41. SOCS2-7 and CIS invariably contain hydrophobic residues at those positions, making it likely they all share a similar structure. It seems likely that SH2 binding, for example to gp130, would affect the position of the N-ESS helix and, through it, the KIR interaction with JAK. Thus, SH2/ligand interaction could co-operatively affect KIR binding or vice-versa. Binding via this mechanism would support the hypothesis that SOCS3 needs to be physically associated with the gp130 receptor in order to bind JAK (Yoshimura et al., 2005).

The SOCS3 structure clearly shows that the PEST motif is located between two secondary structural elements within the SH2 domain on the opposite face to the p-Tyr binding surface. It is not surprising, therefore, that it does not interfere with p-Tyr binding or STAT inhibition. The PEST motif is the most variable region within SOCS3, but given that it is a completely unstructured element, there is remarkable sequence conservation across mammalian species. The SOCS proteins are known to be regulated by a number of processes, including proteolysis (Marine et al., 1999; Sasaki et al., 2003). It is now clear that the PEST motif, in addition to the SOCS box and lysine 6, is an important inducer of protein turnover. Although PEST motifs have been linked to proteasome-mediated degradation in a number of studies (Rechsteiner and Rogers, 1996), our results suggest that it induces degradation via a proteasome independent mechanism. However, when the PEST motif is removed, proteasome-mediated degradation becomes the dominant mechanism of SOCS3 clearance. Different cell types will favour different pathways of proteolytic degradation, and the half-life of SOCS3 can vary from under 5 minutes to over 8 hours, depending on the cell type (Sasaki et al., 2003). However, it is clear that the PEST motif is influencing SOCS3 degradation.

The importance of the N-ESS in SH2 domain function is now clear and suggests a potential mechanism for cooperative binding by the SH2 domain and KIR. The details of the SOCS3 phosphopeptide interaction provide, for the first time, a structural basis for SOCS3 inhibitor design. In addition, the inventors have shown that the PEST motif affects intracellular stability and may be crucial for regulating SOCS3 levels once cytokine signalling has ceased. As well as being functionally significant, the identification of the PEST motif may have important implications for the use of SOCS3 as a therapeutic. Such inhibitors might be used clinically to prolong the action of G-CSF, in the treatment of chemotherapy-induced neutropenia and the mobilisation of haematopoietic stem cells into the peripheral blood. Moreover, SOCS3 also acts as a critical inhibitor of insulin signalling. Thus, SOCS3 inhibitors might potentiate insulin signalling and could be used to treat insulin resistance and type 2 diabetes.

In addition, the inventors have shown that the PEST motif affects intracellular stability and may be crucial for regulating SOCS3 levels once cytokine signalling has ceased. As well as being functionally significant, the identification of the PEST motif may have important implications for the use of SOCS3 as a therapeutic. It has been shown recently that increasing intracellular levels of SOCS3 can suppress LPS-induced inflammation in mice (Jo et al., 2005). A more stable form of SOCS3, such as ΔPEST SOCS3, will obviously enhance these types of intracellular protein therapies. Alternatively, blocking SOCS3 degradation in vivo represents a viable means of treating inflammatory disease.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

All publications discussed above are incorporated herein in their entirety.

This application claims priority from AU 2005906285, the entire contents of which are incorporated herein by reference.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

REFERENCES

Alexander and Hilton (2004) Annu. Rev. Immunol. 22:503-529.
Ball and Alewood (1990) J. Mol. Recognition 3:55.
Becker, S et al. (1998) Nature 394:145-151.
Beddell, (1985) Chem. Soc. Reviews 279.
Bohm and Stahl (1999) M. Med. Chem. Res. 9: 445
Brescia, P J et al. (2002) J Biomol NMR. 23:77-78.
Chen, X P et al. (2002) Proc Natl Acad Sci USA. 99:2175-2180.
Cornilescu, G (1999) J Biomol NMR. 13:289-302.
Croker, B A (2003) Nat Immunol. 4:540-545.
Croker, B A et al. (2004) Immunity 20:153-165.
De Esch, et al. (2001) J. Med. Chem. 44:1666-1674.
Delaglio, F et al. (1995) J Biomol NMR 6:277-293.
DeLano, W L (2004) Abstr Pap Am Chem Soc. 228:U313-U314.
Ewing et al., (2001) J. Comput-Aid. Mol. Design 15: 411.
Farmer (1980) In: Drug Design, E. J. Ariens, ed., Academic Press, New York, v. 10, pp. 119-143.
Freidinger, (1989) Trends Pharmacol. Sci. 10:270.
Friederichs, K et al. (2001) Eur J Biochem. 268:6401-6407.
Gane and Dean (2000) Curr. Opinion Struct. Biol. 10:401.
Good (2001) Current Opinion in Drug Disc. Devel. 5, 301.
Goodford (1984) J. Med. Chem. 27:557.
Goodford (1985) J. Med. Chem. 28:849.
Grucza, R A et al. (1999) Med Res Rev. 19:273-293.
Harper and Rose (1993) Biochemistry 32:7605-7609.
Hilton, D J (1999) Cell Mol Life Sci. 55:1568-1577.
Hilton, D J et al. (1998) Proc Natl Acad Sci USA 95:114-119.
Hirschman et al. (1993) J. Am. Chem. Soc. 115:12550-12568.
Hol, (1986) Angew. Chem. 25:767.
Holm and Sander (1995) Trends Biochem Sci. 478-480.
Hortner, M et al. (2002a) Eur J Biochem. 269:2516-2526.
Hortner, M et al. (2002b) J Immunol. 169:1219-1227.
Horton, R M et al. (1989) Gene 77:61-68.
Ihle, J N et al. (1995) Annu Rev Immunol. 13:369-398.
Jo, D et al. (2005) Nat Med. 11:892-898.
Jones, T A et al. (1991) Acta Cryst. A47:110-119.
Kamura, T et al. (1998) Genes Dev. 12:3872-3881.
Kamura, T et al. (2004) Genes Dev. 18:3055-3065.
Kile, B T et al. (2002) Trends Biochem Sci. 27:235-241.
Kimura, A et al. (2004) J Biol Chem. 279:6905-6910.
Koradi, R et al. (1996) J Mol Graph. 14:51-55.
Kuntz et al., (1982) J. Mol. Biol. 161:269.
Ladbury, J E et al. (1995) Proc Natl Acad Sci USA. 92:3199-3203.
Lang, R et al. (2003) Nat Immunol. 4:546-550.
Langer and Hoffmann, (2001) Current Pharmaceutical Design 7:509.
Laskowski, R A (1996) J Biomol NMR. 8:477-486.
Leonard and O'Shea (1998) Annu Rev Immunol. 16:293-322.
Marine, J C et al. (1999) Cell 98:617-627.
Miller, A D (1990) Human Gene Therapy 1:5-14.
Mills et al. (1997) J Comp Aided Mol Des 11:175-192.
Mills et al. (2001) J Comp Aided Mol Des 15:81-96.
Mizushima and Nagata (1990) Nucleic Acids Res. 18:5322.
Morgan and Gainor (1989) Ann. Rep. Med. Chem. 24:243.
Mori, H et al. (2004) Nat Med. 10:739-743.
Munoz, V et al. (1995) Nat Struct Biol. 2:380-385.
Munson (ed.), Principles of Pharmacology, 1995, Chapman & Hall, Chapter 12.
Naka, T et al. (1997) Nature 387:924-929.
Needleman and Wunsch (1970) J Mol Biol 48:443-453.
Neidhardt, F C et al. (1974) J Bacteriol. 119:736-747.
Nicholson, S E et al. (1999) EMBO J. 375-385.
Nicholson, S E et al. (2000) Proc Natl Acad Sci USA. 97:6493-6498.
Okazaki, Y et al. (2002) Nature 420:563-573.
Pellecchia, M et al. (1999) Nay Struct Biol. 6:336-339.
Perkin, et al. (1995) J Comp Aided Mol Des 9:479-490.
Rarey, M. et al., (1996) J. Mol. Biol. 261:470.
Rechsteiner and Rogers (1996) Trends Biochem Sci. 21:267-271.
Roberts, A W et al. (2001) Proc Natl Acad Sci USA. 98:9324-9329.
Rogers, S (1986) Science 234:364-368.
Sasaki, A et al. (1999) Genes Cells 4:339-351.
Sasaki, A et al. (2000) J Biol Chem. 275:29338-29347.
Sasaki, A et al. (2003) J Biol Chem. 278:2432-2436.
Sawyer, (1995) "Peptidomimetic design and chemical approaches to peptide metabolism", in M D Taylor and G L Amidon, eds., in Peptide-Based Drug Design: Controlling Transport and Metabolism, Ch. 17.
Schmitz, J et al. (2000) J Biol Chem. 275:12848-12856.
Sheridan and Venkataraghavan (1987) Acc. Chem Res. 20:322.
Shi, H et al. (2004) J Biol Chem. 279:34733-34740.
Smith et al. (1994) J. Am. Chem. Soc. 116:9947-9962.
Smith et al. (1995) J. Am. Chem. Soc. 117:11113-11123.
Starr, R et al. (1997) Nature 387:917-921.
Verlinde and Hol, (1984) Structure 2: 577.
Waksman, G et al. (1993) Cell 72:779-790.
Walters, "Computer-Assisted Modeling of Drugs", in Klegerman & Groves (eds.), Pharmaceutical Biotechnology, 1993, Interpharm Press: Buffalo Grove, Ill., pp. 165-174.
Walters et al. (1998) Drug Discovery Today 3: 160.
Ward, A C et al. (1998) Biochim Biophys Acta. 1448:70-76.
Yasukawa, H et al. (1999) EMBO J. 18:1309-1320.
Yasukawa, H et al. (2003) Nat Immunol. 4:551-556.
Yoshimura, A et al. (1995) EMBO J. 14:2816-2826.
Yoshimura, A et al. (2005) Arthritis Res Ther. 7:100-110.
Zhang, J G et al. (1999) Proc Natl Acad Sci USA 96:2071-2076.

The invention claimed is:

1. An isolated suppressor of cytokine signalling 3 (SOCS3) protein which lacks a PEST domain, or has an inactivated PEST domain.

2. The isolated protein of claim 1 which is fused to at least one other polypeptide.

3. A composition comprising the isolated protein of claim 1 and an acceptable carrier.

4. The isolated protein of claim 1 which comprises an amino acid sequence which is at least 95% identical to SEQ ID NO: 3 or SEQ ID NO: 4.

5. The isolated protein of claim 1 which comprises an amino acid sequence which is at least 97% identical to SEQ ID NO: 3 or SEQ ID NO: 4.

6. The isolated protein of claim 1 which comprises an amino acid sequence which is at least 99% identical to SEQ ID NO: 3 or SEQ ID NO: 4.

7. The isolated protein of claim 1 wherein the SOCS3 protein inhibits leukemia-inhibitory factor (LIF)-induced signal transducer and activator of transcription (Stat3) activity.

8. The isolated protein of claim 1 which has a greater half-life than a protein which comprises the amino acid sequence of SEQ ID NO: 1 or SEQ ID NO:2.

9. An isolated protein comprising:
   (i) an amino acid sequence selected from the group consisting of SEQ ID NO: 3 and SEQ ID NO: 4;
   (ii) an amino acid sequence which is at least 80% identical to SEQ ID NO: 3 or SEQ ID NO: 4 and that also lacks a PEST domain or has an inactivated PEST domain; or
   (iii) a biologically active fragment of any one of i) to ii).

10. The isolated protein of claim 9, wherein the protein or biologically active fragment thereof inhibits leukemia-inhibitory factor (LIF)-induced signal transducer and activator of transcription (Stat3) activity.

11. The isolated protein of claim 9 which has greater half-life than a protein which comprises the amino acid sequence of SEQ ID NO: 1 or SEQ ID NO: 2.

* * * * *

SEQUENCE LISTING

<160> NUMBER OF SEQ ID NOS: 17

<210> SEQ ID NO 1
<211> LENGTH: 225
<212> TYPE: PRT
<213> ORGANISM: Mus musculus

<400> SEQUENCE: 1

Met Val Thr His Ser Lys Phe Pro Ala Ala Gly Met Ser Arg Pro Leu
1               5                   10                  15

Asp Thr Ser Leu Arg Leu Lys Thr Phe Ser Ser Lys Ser Glu Tyr Gln
            20                  25                  30

Leu Val Val Asn Ala Val Arg Lys Leu Gln Glu Ser Gly Phe Tyr Trp
        35                  40                  45

Ser Ala Val Thr Gly Gly Glu Ala Asn Leu Leu Leu Ser Ala Glu Pro
    50                  55                  60

Ala Gly Thr Phe Leu Ile Arg Asp Ser Ser Asp Gln Arg His Phe Phe
65                  70                  75                  80

Thr Leu Ser Val Lys Thr Gln Ser Gly Thr Lys Asn Leu Arg Ile Gln
                85                  90                  95

Cys Glu Gly Gly Ser Phe Ser Leu Gln Ser Asp Pro Arg Ser Thr Gln
            100                 105                 110

Pro Val Pro Arg Phe Asp Cys Val Leu Lys Leu Val His His Tyr Met
        115                 120                 125

Pro Pro Pro Gly Thr Pro Ser Phe Ser Leu Pro Pro Thr Glu Pro Ser
    130                 135                 140

Ser Glu Val Pro Glu Gln Pro Ala Gln Ala Leu Pro Gly Ser Thr
145                 150                 155                 160

Pro Lys Arg Ala Tyr Tyr Ile Tyr Ser Gly Gly Glu Lys Ile Pro Leu
                165                 170                 175

Val Leu Ser Arg Pro Leu Ser Ser Asn Val Ala Thr Leu Gln His Leu
            180                 185                 190

Cys Arg Lys Thr Val Asn Gly His Leu Asp Ser Tyr Glu Lys Val Thr
        195                 200                 205

Gln Leu Pro Gly Pro Ile Arg Glu Phe Leu Asp Gln Tyr Asp Ala Pro
    210                 215                 220

Leu
225

<210> SEQ ID NO 2
<211> LENGTH: 225
<212> TYPE: PRT
<213> ORGANISM: Homo sapiens

<400> SEQUENCE: 2

Met Val Thr His Ser Lys Phe Pro Ala Ala Gly Met Ser Arg Pro Leu
1               5                   10                  15

Asp Thr Ser Leu Arg Leu Lys Thr Phe Ser Ser Lys Ser Glu Tyr Gln
            20                  25                  30

Leu Val Val Asn Ala Val Arg Lys Leu Gln Glu Ser Gly Phe Tyr Trp
        35                  40                  45

Ser Ala Val Thr Gly Gly Glu Ala Asn Leu Leu Leu Ser Ala Glu Pro
    50                  55                  60

Ala Gly Thr Phe Leu Ile Arg Asp Ser Ser Asp Gln Arg His Phe Phe
65                  70                  75                  80

```
Thr Leu Ser Val Lys Thr Gln Ser Gly Thr Lys Asn Leu Arg Ile Gln
                85                  90                  95

Cys Glu Gly Gly Ser Phe Ser Leu Gln Ser Asp Pro Arg Ser Thr Gln
            100                 105                 110

Pro Val Pro Arg Phe Asp Cys Val Leu Lys Leu Val His His Tyr Met
        115                 120                 125

Pro Pro Pro Gly Ala Pro Ser Phe Pro Ser Pro Thr Glu Pro Ser
    130                 135                 140

Ser Glu Val Pro Glu Gln Pro Ser Ala Gln Pro Leu Pro Gly Ser Pro
145                 150                 155                 160

Pro Arg Arg Ala Tyr Tyr Ile Tyr Ser Gly Glu Lys Ile Pro Leu
                165                 170                 175

Val Leu Ser Arg Pro Leu Ser Ser Asn Val Ala Thr Leu Gln His Leu
        180                 185                 190

Cys Arg Lys Thr Val Asn Gly His Leu Asp Ser Tyr Glu Lys Val Thr
    195                 200                 205

Gln Leu Pro Gly Pro Ile Arg Glu Phe Leu Asp Gln Tyr Asp Ala Pro
    210                 215                 220

Leu
225

<210> SEQ ID NO 3
<211> LENGTH: 137
<212> TYPE: PRT
<213> ORGANISM: Mus musculus

<400> SEQUENCE: 3

Leu Lys Thr Phe Ser Ser Lys Ser Glu Tyr Gln Leu Val Val Asn Ala
1               5                   10                  15

Val Arg Lys Leu Gln Glu Ser Gly Phe Tyr Trp Ser Ala Val Thr Gly
            20                  25                  30

Gly Glu Ala Asn Leu Leu Leu Ser Ala Glu Pro Ala Gly Thr Phe Leu
        35                  40                  45

Ile Arg Asp Ser Ser Asp Gln Arg His Phe Phe Thr Leu Ser Val Lys
    50                  55                  60

Thr Gln Ser Gly Thr Lys Asn Leu Arg Ile Gln Cys Glu Gly Gly Ser
65                  70                  75                  80

Phe Ser Leu Gln Ser Asp Pro Arg Ser Thr Gln Pro Val Pro Arg Phe
                85                  90                  95

Asp Cys Val Leu Lys Leu Val His His Tyr Met Gly Ser Gly Ser Gly
            100                 105                 110

Ser Gly Ser Ala Tyr Tyr Ile Tyr Ser Gly Glu Lys Ile Pro Leu
        115                 120                 125

Val Leu Ser Arg Pro Leu Ser Ser Asn
    130                 135

<210> SEQ ID NO 4
<211> LENGTH: 177
<212> TYPE: PRT
<213> ORGANISM: Mus musculus

<400> SEQUENCE: 4

Leu Lys Thr Phe Ser Ser Lys Ser Glu Tyr Gln Leu Val Val Asn Ala
1               5                   10                  15

Val Arg Lys Leu Gln Glu Ser Gly Phe Tyr Trp Ser Ala Val Thr Gly
            20                  25                  30
```

Gly Glu Ala Asn Leu Leu Leu Ser Ala Glu Pro Ala Gly Thr Phe Leu
            35                  40                  45

Ile Arg Asp Ser Ser Asp Gln Arg His Phe Phe Thr Leu Ser Val Lys
 50                  55                  60

Thr Gln Ser Gly Thr Lys Asn Leu Arg Ile Gln Cys Glu Gly Gly Ser
 65                  70                  75                  80

Phe Ser Leu Gln Ser Asp Pro Arg Ser Thr Gln Pro Val Pro Arg Phe
                 85                  90                  95

Asp Cys Val Leu Lys Leu Val His His Tyr Met Gly Ser Gly Ser Gly
                100                 105                 110

Ser Gly Ser Ala Tyr Tyr Ile Tyr Ser Gly Gly Glu Lys Ile Pro Leu
            115                 120                 125

Val Leu Ser Arg Pro Leu Ser Ser Asn Val Ala Thr Leu Gln His Leu
130                 135                 140

Cys Arg Lys Thr Val Asn Gly His Leu Asp Ser Tyr Glu Lys Val Thr
145                 150                 155                 160

Gln Leu Pro Gly Pro Ile Arg Glu Phe Leu Asp Gln Tyr Asp Ala Pro
                165                 170                 175

Leu

<210> SEQ ID NO 5
<211> LENGTH: 164
<212> TYPE: PRT
<213> ORGANISM: Rattus norvegicus

<400> SEQUENCE: 5

Leu Lys Thr Phe Ser Ser Lys Ser Glu Tyr Gln Leu Val Val Asn Ala
1               5                   10                  15

Val Arg Lys Leu Gln Glu Ser Gly Phe Tyr Trp Ser Ala Val Thr Gly
            20                  25                  30

Gly Glu Ala Asn Leu Leu Leu Ser Ala Glu Pro Ala Gly Thr Phe Leu
            35                  40                  45

Ile Arg Asp Ser Ser Asp Gln Arg His Phe Phe Thr Leu Ser Val Glu
 50                  55                  60

Thr Gln Ser Gly Thr Lys Asn Leu Arg Ile Gln Cys Glu Gly Gly Ser
 65                  70                  75                  80

Phe Ser Leu Gln Ser Asp Pro Arg Ser Thr Gln Pro Val Pro Arg Phe
                 85                  90                  95

Asp Cys Val Leu Lys Leu Val His His Tyr Met Pro Pro Pro Gly Ala
                100                 105                 110

Pro Ser Phe Ser Leu Pro Pro Thr Glu Pro Ser Phe Glu Val Gln Glu
            115                 120                 125

Gln Pro Pro Ala Gln Ala Leu Pro Gly Gly Thr Pro Lys Arg Ala Tyr
130                 135                 140

Tyr Ile Tyr Ser Gly Gly Glu Lys Ile Pro Leu Val Leu Ser Arg Pro
145                 150                 155                 160

Leu Ser Ser Asn

<210> SEQ ID NO 6
<211> LENGTH: 164
<212> TYPE: PRT
<213> ORGANISM: Canis familiaris

<400> SEQUENCE: 6

Leu Lys Thr Phe Ser Ser Lys Ser Glu Tyr Gln Leu Val Val Asn Ala
1               5                   10                  15

```
Val Cys Lys Leu Gln Glu Ser Gly Phe Tyr Trp Ser Ala Val Thr Gly
            20                  25                  30

Gly Glu Ala Asn Leu Leu Ser Ala Glu Pro Ala Gly Thr Phe Leu
        35                  40                  45

Ile Arg Asp Ser Ser Asp Gln Arg His Phe Phe Thr Leu Ser Val Lys
    50                  55                  60

Thr Gln Ser Gly Thr Lys Asn Leu Arg Ile Gln Cys Glu Gly Gly Ser
65                  70                  75                  80

Phe Ser Leu Gln Ser Asp Pro Arg Ser Thr Gln Pro Val Pro Arg Phe
                85                  90                  95

Asp Cys Val Leu Lys Leu Val His His Tyr Met Pro Pro Gly Ala
            100                 105                 110

Pro Ser Phe Pro Ala Pro Thr Glu Pro Ser Glu Val Ser Glu
        115                 120                 125

Gln Pro Pro Ser Gln Pro Leu Pro Gly Asn Pro Arg Arg Ala Tyr
    130                 135                 140

Tyr Ile Tyr Ser Gly Gly Glu Lys Ile Pro Leu Val Leu Ser Arg Pro
145                 150                 155                 160

Leu Ser Ser Asn

<210> SEQ ID NO 7
<211> LENGTH: 168
<212> TYPE: PRT
<213> ORGANISM: Bos taurus

<400> SEQUENCE: 7

Leu Lys Thr Phe Ser Ser Lys Ser Glu Tyr Gln Leu Val Val Asn Ala
1               5                   10                  15

Val Arg Lys Leu Gln Glu Ser Gly Phe Tyr Trp Ser Thr Val Thr Gly
            20                  25                  30

Gly Glu Ala Asn Leu Leu Ser Ala Glu Pro Ala Gly Thr Phe Leu
        35                  40                  45

Ile Arg Asp Ser Ser Asp Gln Arg His Phe Phe Thr Leu Ser Val Lys
    50                  55                  60

Thr Gln Ser Gly Thr Lys Asn Leu Arg Ile Gln Cys Glu Gly Gly Ser
65                  70                  75                  80

Phe Ser Leu Gln Ser Asp Pro Arg Ser Thr Gln Pro Val Pro Arg Phe
                85                  90                  95

Asp Cys Val Leu Lys Leu Val His His Tyr Met Pro Ala Ala Gly Ala
            100                 105                 110

Pro Ser Phe Ser Gln Pro Pro Ala Glu Pro Ser Ser Ser Pro Ser Ser
        115                 120                 125

Glu Val Pro Glu Gln Pro Pro Ala Gln Pro Leu Ser Gly Asn Pro Pro
    130                 135                 140

Arg Arg Ala Tyr Tyr Ile Tyr Ser Gly Gly Glu Lys Ile Pro Leu Val
145                 150                 155                 160

Leu Ser Arg Pro Leu Ser Ser Asn
                165

<210> SEQ ID NO 8
<211> LENGTH: 148
<212> TYPE: PRT
<213> ORGANISM: Gallus gallus
```

<400> SEQUENCE: 8

Leu Lys Thr Phe Ser Ser Lys Ser Glu Tyr Gln Leu Val Val Asn Thr
1               5                   10                  15

Val Arg Lys Leu Gln Glu Ser Gly Phe Tyr Trp Ser Thr Val Thr Gly
            20                  25                  30

Gly Glu Ala Asn Val Leu Leu Ser Ala Glu Pro Ala Gly Thr Phe Leu
        35                  40                  45

Ile Arg Asp Ser Ser Asp Gln Arg His Phe Phe Thr Leu Ser Val Lys
    50                  55                  60

Thr Glu Ser Gly Thr Lys Asn Leu Arg Ile Gln Cys Glu Gly Gly Ser
65                  70                  75                  80

Phe Ser Leu Gln Ser Asp Pro Arg Ser Ser Gln Pro Val Pro Arg Phe
                85                  90                  95

Asp Cys Val Leu Lys Leu Val His His Tyr Met Pro Thr Pro Cys
                100                 105                 110

Ala Gly Pro Lys Gln Pro Gly Gly Ala Leu His Pro Lys Arg Thr Tyr
            115                 120                 125

Tyr Ile Tyr Ser Gly Gly Glu Lys Ile Pro Leu Val Leu Ser Arg Pro
130                 135                 140

Leu Ser Ser Ser
145

<210> SEQ ID NO 9
<211> LENGTH: 140
<212> TYPE: PRT
<213> ORGANISM: Xenopus tropicalis

<400> SEQUENCE: 9

Leu Lys Thr Phe Ser Ser Cys Ser Glu Tyr Asn Leu Val Leu Thr Ala
1               5                   10                  15

Val Arg Lys Leu Gln Glu Ser Gly Phe Tyr Trp Ser Thr Val Thr Gly
            20                  25                  30

Ser Gln Ala Asn Leu Leu Leu Ser Thr Glu Pro Ala Gly Thr Phe Leu
        35                  40                  45

Ile Arg Asp Ser Ser Asp Arg Arg His Phe Phe Thr Leu Ser Val Lys
    50                  55                  60

Thr Glu Ser Gly Thr Lys Asn Leu Arg Ile Gln Cys Glu Pro Cys Gly
65                  70                  75                  80

Phe Ser Leu Gln Thr Glu Pro Arg Ser Ala Gln Pro Val Pro Arg Phe
                85                  90                  95

Asp Cys Val Leu Lys Leu Leu Cys His Tyr Met Pro Thr Lys Asp Ser
                100                 105                 110

Ser Ser Gly Ser Lys Arg Ala Tyr Tyr Ile Tyr Ser Gly Gly Glu Arg
            115                 120                 125

Val Pro Leu Leu Leu Ser Arg Pro Leu Ser Thr Asn
130                 135                 140

<210> SEQ ID NO 10
<211> LENGTH: 8
<212> TYPE: PRT
<213> ORGANISM: Artificial
<220> FEATURE:
<223> OTHER INFORMATION: PEST replacement construct

<400> SEQUENCE: 10

Gly Ser Gly Ser Gly Ser Gly Ser
1               5

```
<210> SEQ ID NO 11
<211> LENGTH: 15
<212> TYPE: PRT
<213> ORGANISM: Artificial
<220> FEATURE:
<223> OTHER INFORMATION: Phosphotyrosine peptide gp130
<220> FEATURE:
<221> NAME/KEY: Phosphotyrosine
<222> LOCATION: (8)..(8)

<400> SEQUENCE: 11

Ser Thr Ala Ser Thr Val Glu Tyr Ser Thr Val Val His Ser Gly
1               5                   10                  15

<210> SEQ ID NO 12
<211> LENGTH: 164
<212> TYPE: PRT
<213> ORGANISM: Mus musculus

<400> SEQUENCE: 12

Leu Lys Thr Phe Ser Ser Lys Ser Glu Tyr Gln Leu Val Val Asn Ala
1               5                   10                  15

Val Arg Lys Leu Gln Glu Ser Gly Phe Tyr Trp Ser Ala Val Thr Gly
            20                  25                  30

Gly Glu Ala Asn Leu Leu Ser Ala Glu Pro Ala Gly Thr Phe Leu
        35                  40                  45

Ile Arg Asp Ser Ser Asp Gln Arg His Phe Phe Thr Leu Ser Val Lys
    50                  55                  60

Thr Gln Ser Gly Thr Lys Asn Leu Arg Ile Gln Cys Glu Gly Gly Ser
65                  70                  75                  80

Phe Ser Leu Gln Ser Asp Pro Arg Ser Thr Gln Pro Val Pro Arg Phe
                85                  90                  95

Asp Cys Val Leu Lys Leu Val His His Tyr Met Pro Pro Pro Gly Thr
                100                 105                 110

Pro Ser Phe Ser Leu Pro Pro Thr Glu Pro Ser Ser Glu Val Pro Glu
            115                 120                 125

Gln Pro Pro Ala Gln Ala Leu Pro Gly Ser Thr Pro Lys Arg Ala Tyr
        130                 135                 140

Tyr Ile Tyr Ser Gly Gly Glu Lys Ile Pro Leu Val Leu Ser Arg Pro
145                 150                 155                 160

Leu Ser Ser Asn

<210> SEQ ID NO 13
<211> LENGTH: 164
<212> TYPE: PRT
<213> ORGANISM: Homo sapiens

<400> SEQUENCE: 13

Leu Lys Thr Phe Ser Ser Lys Ser Glu Tyr Gln Leu Val Val Asn Ala
1               5                   10                  15

Val Arg Lys Leu Gln Glu Ser Gly Phe Tyr Trp Ser Ala Val Thr Gly
            20                  25                  30

Gly Glu Ala Asn Leu Leu Ser Ala Glu Pro Ala Gly Thr Phe Leu
        35                  40                  45

Ile Arg Asp Ser Ser Asp Gln Arg His Phe Phe Thr Leu Ser Val Lys
    50                  55                  60

Thr Gln Ser Gly Thr Lys Asn Leu Arg Ile Gln Cys Glu Gly Gly Ser
65                  70                  75                  80
```

-continued

```
Phe Ser Leu Gln Ser Asp Pro Arg Ser Thr Gln Pro Val Pro Arg Phe
                85                  90                  95

Asp Cys Val Leu Lys Leu Val His His Tyr Met Pro Pro Gly Ala
            100                 105                 110

Pro Ser Phe Pro Ser Pro Thr Glu Pro Ser Ser Glu Val Pro Glu
        115                 120                 125

Gln Pro Ser Ala Gln Pro Leu Pro Gly Ser Pro Arg Arg Ala Tyr
    130                 135                 140

Tyr Ile Tyr Ser Gly Gly Glu Lys Ile Pro Leu Val Leu Ser Arg Pro
145                 150                 155                 160

Leu Ser Ser Asn

<210> SEQ ID NO 14
<211> LENGTH: 8
<212> TYPE: PRT
<213> ORGANISM: Artificial
<220> FEATURE:
<223> OTHER INFORMATION: Flag epitope tag

<400> SEQUENCE: 14

Asp Tyr Lys Asp Asp Asp Asp Lys
1               5

<210> SEQ ID NO 15
<211> LENGTH: 411
<212> TYPE: DNA
<213> ORGANISM: Artificial
<220> FEATURE:
<223> OTHER INFORMATION: Sequence encoding deltaPEST SOCS-3(22-185).

<400> SEQUENCE: 15
ctgaaaacct ttagcagcaa aagcgaatat cagctggtgg tgaacgcggt gcgcaaactg      60
caggaaagcg gctttttattg gagcgcggtg accggcggcg aagcgaacct gctgctgagc    120
gcggaaccgg cgggcaccttt tctgattcgc gatagcagcg atcagcgcca ttttttttacc   180 ctgagcgtga aacccagag cggcaccaaa aacctgcgca ttcagtgcga aggcggcagc      240
tttagcctgc agagcgatcc gcgcagcacc cagccggtgc cgcgctttga ttgcgtgctg    300
aaactggtgc atcattatat gggcagcggc agcggcagcg gcagcgcgta ttatatttat    360
agcggcggcg aaaaaattcc gctggtgctg agccgcccgc tgagcagcaa c              411

<210> SEQ ID NO 16
<211> LENGTH: 531
<212> TYPE: DNA
<213> ORGANISM: Artificial
<220> FEATURE:
<223> OTHER INFORMATION: Sequence encoding deltaPEST SOCS-3(22-225)

<400> SEQUENCE: 16
ctgaaaacct ttagcagcaa aagcgaatat cagctggtgg tgaacgcggt gcgcaaactg      60
caggaaagcg gctttttattg gagcgcggtg accggcggcg aagcgaacct gctgctgagc    120
gcggaaccgg cgggcaccttt tctgattcgc gatagcagcg atcagcgcca ttttttttacc   180 ctgagcgtga aacccagag cggcaccaaa aacctgcgca ttcagtgcga aggcggcagc      240
tttagcctgc agagcgatcc gcgcagcacc cagccggtgc cgcgctttga ttgcgtgctg    300
aaactggtgc atcattatat gggcagcggc agcggcagcg gcagcgcgta ttatatttat    360
agcggcggcg aaaaaattcc gctggtgctg agccgcccgc tgagcagcaa cgtggcgacc    420
```

-continued

```
ctgcagcatc tgtgccgcaa aaccgtgaac ggccatctgg atagctatga aaaagtgacc    480
cagctgccgg gcccgattcg cgaatttctg gatcagtatg atgcgccgct g             531
```

<210> SEQ ID NO 17
<211> LENGTH: 12
<212> TYPE: PRT
<213> ORGANISM: Artificial
<220> FEATURE:
<223> OTHER INFORMATION: Cell-penetrating motif

<400> SEQUENCE: 17

```
Ala Ala Val Leu Leu Pro Val Leu Leu Ala Ala Pro
1               5                   10
```